(12) United States Patent
Choi et al.

(10) Patent No.: US 9,095,613 B2
(45) Date of Patent: Aug. 4, 2015

(54) PHOTOSENSITIZER-METAL NANOPARTICLE CHARGE COMPLEX AND COMPOSITION CONTAINING THE COMPLEX FOR PHOTODYNAMIC THERAPY OR DIAGNOSIS

(75) Inventors: Yong-Doo Choi, Gyeonggi-do (KR); Bo-Seung Jang, Gyeonggi-do (KR); Jin-Young Park, Gyeonggi-do (KR); Jung-Im Lee, Gyeonggi-do (KR); In-Hoo Kim, Gyeonggi-do (KR)

(73) Assignee: NATIONAL CANCER CENTER, Gyeonggi-Do (KR)

( * ) Notice: Subject to any disclaimer, the term of this patent is extended or adjusted under 35 U.S.C. 154(b) by 399 days.

(21) Appl. No.: 12/673,122

(22) PCT Filed: Oct. 28, 2009

(86) PCT No.: PCT/KR2009/006263
§ 371 (c)(1),
(2), (4) Date: Feb. 11, 2010

(87) PCT Pub. No.: WO2011/049256
PCT Pub. Date: Apr. 28, 2011

(65) Prior Publication Data
US 2012/0014874 A1    Jan. 19, 2012

(51) Int. Cl.
| | | |
|---|---|---|
| A61B 10/00 | (2006.01) |
| A61B 5/00 | (2006.01) |
| A61B 8/00 | (2006.01) |
| A61K 41/00 | (2006.01) |
| A61K 33/24 | (2006.01) |
| A61K 49/00 | (2006.01) |

(52) U.S. Cl.
CPC ............ A61K 41/0071 (2013.01); A61K 33/24 (2013.01); A61K 49/0036 (2013.01); A61K 49/0065 (2013.01); Y10T 428/2991 (2015.01)

(58) Field of Classification Search
CPC . A61K 49/00; A61K 49/001; A61K 49/0017; A61K 49/0036; A61K 41/00; A61K 41/0057; A61K 33/24; Y10T 428/2991
USPC ............... 424/1.11, 1.49, 1.65, 1.73, 9.1, 9.3, 424/9.361, 9.362, 9.363, 9.364, 9.6, 9.61, 424/489, 490, 493, 497, 499, 178.1; 540/1, 540/121, 145, 450; 544/1; 546/1; 548/100, 548/400; 428/403; 514/1.1, 44 A, 44 R, 54, 514/55, 56, 410; 525/326.9, 330.2, 450; 530/300, 330, 391.7; 536/20, 21, 23.1, 536/24.5, 123.1
See application file for complete search history.

(56) References Cited

U.S. PATENT DOCUMENTS

| | | | | |
|---|---|---|---|---|
| 6,936,279 | B2 * | 8/2005 | Guerra-Santos et al. | ...... 424/489 |
| 7,964,568 | B2 * | 6/2011 | Beck et al. | ....................... 514/25 |
| 8,268,048 | B2 * | 9/2012 | Subramaniam et al. | ......... 95/138 |
| 8,709,531 | B2 * | 4/2014 | Miller | ............................. 427/74 |
| 8,746,075 | B2 * | 6/2014 | Eichhorn et al. | ................. 73/777 |
| 2001/0022963 | A1 | 9/2001 | Klaveness et al. | |
| 2004/0179800 | A1 * | 9/2004 | Walker et al. | ................. 385/128 |
| 2005/0136638 | A1 * | 6/2005 | Voss-Kehl et al. | ............ 438/610 |
| 2009/0060840 | A1 | 3/2009 | Boyes et al. | |
| 2010/0140112 | A1 | 6/2010 | Seo et al. | |

FOREIGN PATENT DOCUMENTS

| | | |
|---|---|---|
| KR | 10-2007-0118501 A | 12/2007 |
| KR | 10-0809402 B1 | 2/2008 |

OTHER PUBLICATIONS

Golub et al., Science, Oct. 15, 1999, pp. 531-537.*
Hone et al Langmuir, 2002, vol. 18, pp. 2985-2987.*
Lahav et al, J. Am. Chem. Soc., 2000, vol. 122, pp. 11480-11487.*
Bechet et al., "Nanoparticles as vehicles for delivery of photodynamic therapy agents," *Trends Biotechnol*, 2008, 26(11):612-621.
Hone et al., "Generation of Cytotoxic Singlet Oxygen via Phthalocyanine-Stabilized Gold Nanoparticles: A Potential Delivery Vehicle for Photodynamic Therapy," *Langmuir*, 2002, 18(8):2985-2987.
Tsay et al., "Singlet Oxygen Production by Peptide-Coated Quantum Dot-Photosensitizer Conjugates," *J Am Chem Soc*, 2007, 129(21):6865-6871.
International Search Report for PCT/KR2009/006263, dated Jan. 28, 2011 (4 pages).

(Continued)

*Primary Examiner* — D L Jones
(74) *Attorney, Agent, or Firm* — Foley & Lardner LLP; Michael Morency

(57) ABSTRACT

Provided are a photosensitizer-metal nanoparticle charge complex and a composition for photodynamic therapy or diagnosis containing the same. The complex includes a metal nanoparticle, a photosensitizer charged with a first charge, and a linker bound to the metal nanoparticle and charged with a second charge having an opposite polarity to the first charge. During circulation in blood, the photosensitizer-metal nanoparticle charge complex is maintained in a complex type, and thus duration of a side effect of photosensitivity can be reduced. In a tumor tissue, the complex is specifically accumulated, but in a normal tissue, it is difficult for the complex to penetrate. Thus, the complex can selectively destroy the tumor tissue. Moreover, selective fluorescence in the tumor tissue can provide further improvement in accuracy of diagnosing a tumor using the complex.

17 Claims, 25 Drawing Sheets

(56) References Cited

OTHER PUBLICATIONS

Agostinis, "Photodynamic Therapy of Cancer: An Update", American Cancer Society, Inc., vol. 61, No. 4, Jul./Aug. 2011.

Zhirui Guo, et al., "Facile synthesis of micrometer-sized gold nanoplates through an aniline-assisted route in ethylene glycol solution", Colloids and Surfaces A: Physicochem. Eng. Aspects 278 (2006) 33-38.

* cited by examiner

[AlPcS₄ in SCC7 cell]

[ GNR/AlPcS$_4$ Complex in SCC7 cell ]

SEQUENCE LISTING

```
<160> NUMBER OF SEQ ID NOS: 1

<210> SEQ ID NO 1
<211> LENGTH: 5
<212> TYPE: PRT
<213> ORGANISM: Artificial Sequence
<220> FEATURE:
<223> OTHER INFORMATION: linking polypeptide

<400> SEQUENCE: 1

Arg Arg Leu Ala Cys
 1               5
```

PHOTOSENSITIZER-METAL NANOPARTICLE CHARGE COMPLEX AND COMPOSITION CONTAINING THE COMPLEX FOR PHOTODYNAMIC THERAPY OR DIAGNOSIS

RELATED APPLICATIONS

This application is the U.S. National Stage of International Application No. PCT/009/006263, filed Oct. 28, 2009, which claims priority to the Republic of Korea Application No. 2009/101468, filed on Oct. 23, 2009. The entire contents of the above applications are incorporated herein by reference.

TECHNICAL FIELD

The present invention relates to a photosensitizer, and more particularly, to a photosensitizer-metal nanoparticle charge complex and a composition for photodynamic therapy or diagnosis containing the same.

BACKGROUND ART

Photodynamic therapy using a photosensitizer has attracted attention as a form of therapy capable of overcoming sequelae of cancer and side effects of conventional cancer treatments such as surgery, radiation therapy, and drug therapy.

The photosensitizer is excited by irradiation with light at a specific wavelength, and reacts with a surrounding substrate or oxygen, thereby producing a reactive oxygen species, resulting in apoptosis or necrosis of surrounding tumor cells.

However, a first generation photosensitizer currently used for caner treatment, Photofrin, has two major disadvantages, which are a low molar absorption coefficient of 1170 $M^{-1}$ $cm^{-1}$ at a wavelength of 630 nm, and a more than 6-week-lasting side effect of skin photosensitivity. Skin photosensitivity refers to a side effect of killing normal cells of skin or eyes of a patient by photosensitizers non-specifically accumulated and remaining after administration of the photosensitizer when the patient is exposed to light. Since Photofrin is easily accumulated non-specifically in cells of the skin or eyes due to hydrophobicity, it is known that the side effect of skin photosensitivity lasts relatively long.

To overcome the disadvantages of Photofrin, a second generation photosensitizer, Foscan, has been developed. Foscan has a high molar absorption coefficient of 30000 $M^{-1}$ $cm^{-1}$ at 652 nm, and thus exhibits a 200-fold increase in efficiency of the photodynamic therapy, compared to Photofrin. However, since Foscan also has hydrophobicity, it is not able to significantly reduce the side effect of the skin photosensitivity.

To overcome such a side effect of the skin photosensitivity, a hydrophilic second generation photosensitizer, mono-L-aspartyl chlorine e6 (NPe6), which is in phase III clinical trial, has been developed. Mono-L-aspartyl chlorine e6 is a photosensitizer to which four carboxyl groups are introduced, which greatly reduces the duration of the side effect of the skin photosensitivity to 1 week because of the hydrophilicity of the carboxyl groups. However, the photosensitizer having the carboxyl groups is negatively charged and difficult to be taken up into cancer cells even upon reaching a cancer tissue. Moreover, the photosensitizer having the hydrophilic carboxyl group can be excreted rapidly from a body through the urinary system. Accordingly, to be accumulated in a tumor tissue in an appropriate concentration, the hydrophilic photosensitizer should be administered at a much higher dose than the hydrophobic photosensitizer. As a result, an amount of the photosensitizer non-specifically accumulated in the normal tissue cannot be reduced to a satisfactory level, and thus the second generation hydrophilic photosensitizer still has the side effect of the skin photosensitivity.

DISCLOSURE

Technical Problem

The present invention is directed to a photosensitizer-metal nanoparticle charge complex, in which a photodynamic reaction more selectively occurs in a target lesion, and thus a side effect of the reaction may be reduced, and a composition for photodynamic therapy or diagnosis containing the same.

Technical Solution

One aspect of the present invention provides a photosensitizer-metal nanoparticle charge complex. The complex includes a metal nanoparticle, negatively or positively charged photosensitizers, and linkers having the opposite charge to the photosensitizer and bound to the metal nanoparticle.

Another aspect of the present invention provides a composition for photodynamic therapy or diagnosis. The composition includes a photosensitizer-metal nanoparticle charge complex and a pharmaceutically available carrier.

Advantageous Effects

According to the present invention, a photosensitizer-metal nanoparticle charge complex has a photosensitizer bound to a metal nanoparticle by charge-charge interaction, and as time goes on, the photosensitizer is slowly dissociated from the metal nanoparticle. Thus, during circulation of the complex administered in vivo in blood, the photosensitizer cannot be dissociated from the metal nanoparticle such that it is maintained in a complex type. While the photosensitizer constitutes a complex with the metal nanoparticle, even when exposed to light, fluorescence and production of reactive oxygen (species) are inhibited.

Such a photosensitizer-metal nanoparticle charge complex cannot be easily excreted from a body through the urinary system because the complex is relatively large in size, compared to the photosensitizer itself. In addition, it is difficult for the photosensitizer-metal nanoparticle charge complex to penetrate into a normal tissue which has relatively tight walls of blood vessels because of the relatively large size of the complex. However, it can selectively penetrate a leaky wall of a newly formed blood vessel, which is present in a tumor, so as to permeate into a tumor tissue. Moreover, the photosensitizer-metal nanoparticle charge complex can be accumulated in the tumor and stay long because of the lack of lymphatic drainage in the tumor. As a result, the photosensitizer-metal nanoparticle charge complex can be selectively accumulated in the tumor tissue. The photosensitizer-metal nanoparticle charge complex can be almost electrically neutral since components having opposite charges to each other bind to each other by charge interaction. Thus, the photosensitizer-metal nanoparticle charge complex can very easily enter into tumor cells by endocytosis, compared to a negatively or positively charged photosensitizer. Accordingly, the photosensitizer-metal nanoparticle charge complex is capable of being easily accumulated in the tumor cells.

While being circulated in the blood, since the photosensitizer-metal nanoparticle charge complex is maintained in the form of a complex, and it is difficult to penetrate into a normal tissue, duration of the side effect of the photosensitivity can be reduced. Further, the photosensitizer released from the photosensitizer-metal nanoparticle charge complex, which has been specifically accumulated in the tumor tissue, can effectively destroy the tumor tissue through the photodynamic therapy. In addition, selective fluorescence exhibited in the tumor tissue can provide an improvement in accuracy of tumor diagnosis using the above complex.

Effects of the present invention will not be limited to the above-described effects, and other effects, which are not described herein, will be clearly understood from the accompanying claims by those skilled in the art.

MODE FOR INVENTION

Hereinafter, exemplary embodiments of the present invention will be described in detail. However, the present invention is not limited to the exemplary embodiments disclosed below, but can be implemented in various types. Therefore, the present exemplary embodiments are provided for complete disclosure of the present invention and to fully inform the scope of the present invention to those ordinarily skilled in the art.

Photosensitizer-Metal Nanoparticle Charge Complex

Figure 1:
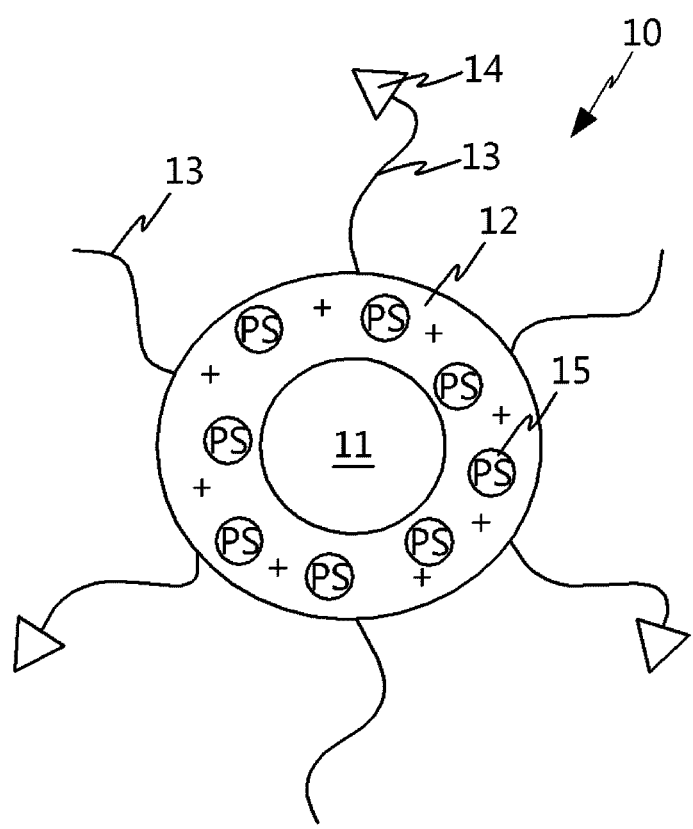
FIG. 1 is a schematic view of a photosensitizer-metal nanoparticle charge complex according to an exemplary embodiment of the present invention.

FIG. 1 is a schematic view of a photosensitizer-metal nanoparticle charge complex according to an exemplary embodiment of the present invention.

Referring to FIG. 1, a photosensitizer-metal nanoparticle charge complex 10 includes a metal nanoparticle 11, a photosensitizer 15 charged with a first charge, and a linker 12 bound to the metal nanoparticle 11 and charged with a second charge that has an opposite polarity to the first charge.

The metal nanoparticle 11 is a nanoparticle at least having a length extending in one direction of several to several hundreds of nanometers, which may be composed of a metal capable of transferring resonance energy with the photosensitizer 15. The metal constituting the metal nanoparticle 11 may be gold (Au), silver (Ag), copper (Cu), platinum (Pt), palladium (Pd), nickel (Ni), iron (Fe) or a combination thereof.

In one exemplary embodiment, the metal constituting the metal nanoparticle 11 may be Au, which has a molar absorption coefficient of $10^9$ or higher and thus may absorb light 10000 times more effectively than the photosensitizer 15, and a surface of which a material may be easily introduced to. The metal nanoparticle 11 may have the shape of a sphere, rod, pyramid, star, or core-shell. Such a metal nanoparticle 11 may absorb light in various ranges of wavelength depending on its components, shape or size. Thus, to overlap a fluorescence spectrum of the photosensitizer 15 with an absorption spectrum of the metal nanoparticle 11, the components, shape or size of the metal nanoparticle 11 may be adjusted.

The linker 12 may be a polypeptide or biocompatible polymer, which is bound to the metal nanoparticle 11 chemically or by charge interaction and can bind the photosensitizer 15 by the charge interaction.

As an example, the linker 12 may be a polypeptide including arginine (Arg), lysine (Lys) or histidine (His) having a cation as a residue in a polar solvent; or aspartic acid (Asp) or glutamic acid (Glu) having an anion as a residue in a polar solvent. Here, the linker 12 may be bound to both the metal nanoparticle 11 and the photosensitizer 15 by the anion or cation through charge interaction. Alternatively, the linker 12 may contain an amino acid having an anion or cation as a residue on one terminal and cysteine having a thiol group as a residue on the other terminal. Here, the linker 12 may be chemically adsorbed to a surface of the metal nanoparticle 11 by a thiol-metal bond and may bind the photosensitizer 15 thereto by the charge interaction.

In another example, the linker 12 may be a biocompatible polymer, which includes carboxylic acid or a salt thereof, sulfonic acid or a salt thereof, or an amine group as a substituent. The substituent may be ionized to a carboxylate anion, a sulfonate anion, or an ammonium cation in a polar solvent. Such a biocompatible polymer may be a polysaccharide; heparin or a derivative thereof; hyaluronic acid or a derivative thereof; gelatin or a derivative thereof; poly(acrylic acid) or a derivative thereof; polylysine or a derivative thereof; poly(ethylene imine) or a derivative thereof; chitosan or a derivative thereof; or polyvinylpyrrolidone or a derivative thereof, which has carboxylic acid or a salt thereof, or sulfonic acid or a salt thereof as a substituent. Here, because of the anion or cation, the linker 12 may be bound to both the metal nanoparticle 11 and the photosensitizer 15 by charge interaction. Alternatively, the linker 12 may include an anion or cation as a substituent on one terminal, and a thiol group as a substituent on the other terminal. Here, the linker 12 may be chemically adsorbed to a surface of the nanoparticle 11 by a thiol-metal bond and may bind the photosensitizer 15 thereto by the charge interaction.

The linker 12 may have the appropriate number of amino acids, which constitute the linker 12, or the appropriate number of carbon atoms such that the photosensitizer 15 is spaced within about 20 nm from the surface of the metal nanoparticle 11.

The photosensitizer 15 may be a porphyrin-based compound or a non-porphyrin compound, the compound may be in the form of a free base or metal complex. Examples of the porphyrin-based compound may include porphyrin derivatives; reduced porphyrins, in which at least one pyrrole constituting porphyrin is reduced into pyrroline, such as chlorin and bacteriochlorin; and porphyrin analogues such as phthalocyanine and naphthalocyanine Examples of the non-porphyrin compound may include hypericin, rhodamine, rose Bengal, psoralen, a phenothiazinium dye, or merocyanine. Such the photosensitizer 15 may include carboxylic acid or a salt thereof, sulfonic acid or a salt thereof, or an amine group as a substituent. The substituent of the photosensitizer 15 may be ionized to a carboxylate anion, a sulfonate anion or an ammonium cation in a polar solvent, and bound to the linker 12 by the charge interaction. To this end, the charge (or ion) contained in the photosensitizer 15 should have an opposite polarity to the charge (or ion) contained in the linker 12 as described above.

The photosensitizer 15 is non-toxic in a ground energy state, whereas it is excited to a singlet energy state when light having a specific wavelength is absorbed. Majority of the photosensitizers in the singlet excited state transit to a triplet excited state through intersystem crossing, and others return to the ground energy state by emitting energy in the form of fluorescence. The photosensitizer in the singlet or triplet excited state produces a reactive oxygen species such as singlet oxygen, oxygen radical, super oxide or peroxide by reaction with a surrounding substrate or oxygen. The produced reactive oxygen species may result in apoptosis or necrosis of surrounding tumor cells.

In consideration of light penetration possibility into a tissue and production efficiency of the reactive oxygen species, the photosensitizer 15 may be a material excited by light having a wavelength of 450 to 950 nm, and preferably, 600 to 900 nm.

When the photosensitizer 15 is bound to the linker 12 by the charge interaction, that is, the photosensitizer 15 and metal nanoparticle 11 linked by the linker 12 make the photosensitizer-metal nanoparticle charge complex 10, the photosensitizer 15 can be adjacent to the metal nanoparticle 11.

And when the photosensitizer-metal nanoparticle charge complex 10 is exposed to light having a specific wavelength, energy transfer may occur onto the surface of the metal nanoparticle 11 from the photosensitizer 15 in the singlet excited state. Thus, the photosensitizer 15 in the singlet energy state is not only unable to emit fluorescence, but also cannot produce a reactive oxygen species. As a result, the photosensitizer-metal nanoparticle charge complex 10 in which the metal nanoparticle 11 is adjacent to the photosensitizer 15 by the linker 12 cannot exhibit cytotoxicity.

The photosensitizer-metal nanoparticle charge complex 10 may further contain a hydrophilic polymer 13. The hydrophilic polymer 13 may be bound to the metal nanoparticle 11 or the linker 12. The hydrophilic polymer 13 may be poly (alkylene glycol) having biocompatibility such as low immunogenicity. The poly(alkylene glycol) may be polyethylene glycol (PEG); methoxy polyethylene glycol (MPEG); methoxy polypropylene glycol; a copolymer of PEG and methoxy polypropylene glycol; dextran; hyaluronic acid; a copolymer of polylactic acid and polyglycolic acid; PEG-diacid; PEG monoamine; MPEG monoamine; MPEG hydrazide; MPEG imidazole; or a copolymer of at least two selected from the group consisting of PEG, methoxy polypropylene glycol, PEG-diacid, PEG monoamine, MPEG monoamine, MPEG hydrazide, and MPEG imidazole. Alternatively, the hydrophilic polymer 13 may be a copolymer of poly(alkylene glycol) and another polymer, such as a copolymer of PEG and polypeptide, PEG and polysaccharide, PEG and polyamidoamine, PEG and polyethyleneimine, or PEG and polynucleotide.

The hydrophilic polymer 13 may inhibit non-specific adsorption of serum in the blood onto a surface of the complex 10 because of the low immunogenicity, and inhibit removal of the complex 10 through the urinary system. As a result, a half-life of the photosensitizer-metal nanoparticle charge complex 10 in the blood may be increased compared to the second generation hydrophilic photosensitizer. In addition, the hydrophilic polymer 13 may further increase the hydrodynamic volume of the complex 10, and thus the complex 10 cannot penetrate the wall of the blood vessel in the normal tissue. However the complex 10 having the hydrophilic polymer 13 can penetrate a newly-formed leaky blood vessel existing in the tumor. Thus, the complex 10 to which the hydrophilic polymer 13 is introduced may be specifically accumulated in the tumor tissue.

The photosensitizer-metal nanoparticle charge complex 10 may further contain a tumor targeting part 14. The tumor targeting part 14 may be bound to a terminal of the hydrophilic polymer 13 or the linker 12. The tumor targeting part 14 may be an antibody, folic acid, a peptide ligand having at least two amino acids, a cyclic arginine-glycine-aspartic acid (RGD) peptide, a RNA aptamer, siRNA, or an oligonucleotide, which specifically reacts to the tumor. When the tumor targeting part 14 is introduced, the photosensitizer-metal nanoparticle charge complex 10 may be more specifically accumulated in a tumor such as cancer.

Figure 2:
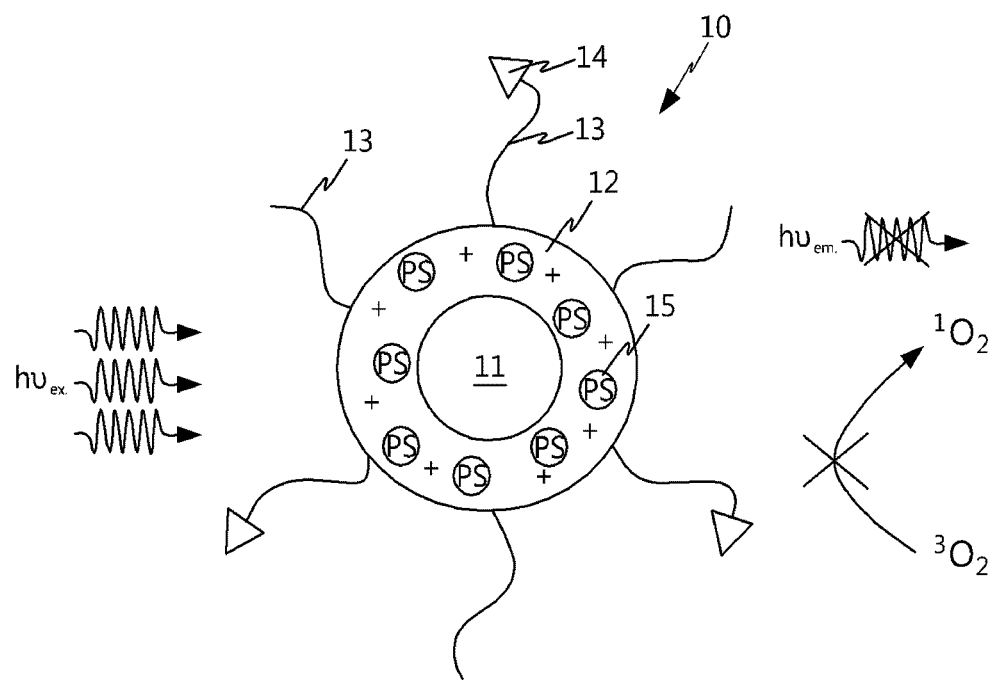
FIGS. 2 and 3 are schematic views illustrating light-induced reactions of the photosensitizer-metal nanoparticle charge complex according to an exemplary embodiment of the present invention.
Figure 3:
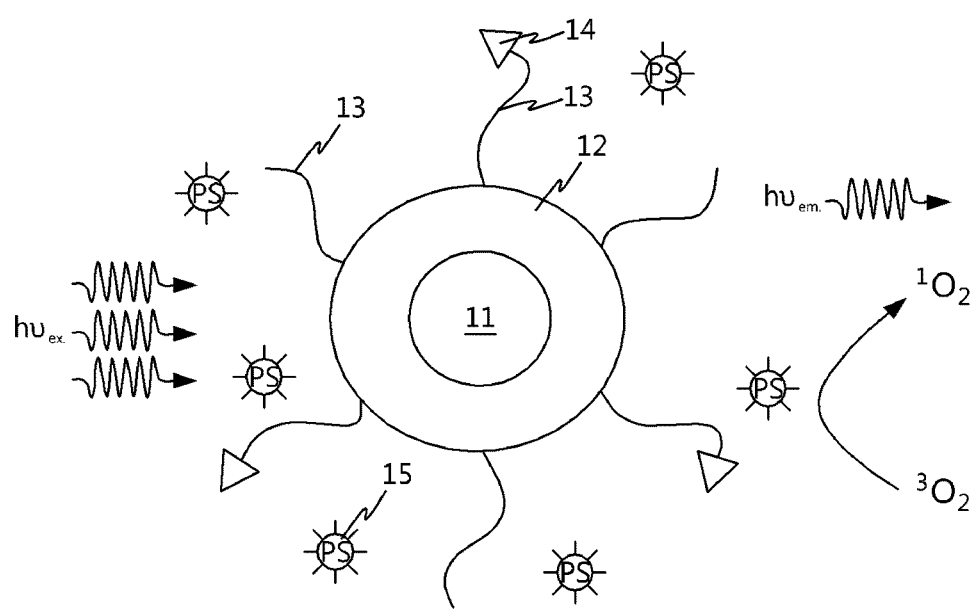

FIGS. 2 and 3 are schematic views illustrating light-induced reactions of the photosensitizer-metal nanoparticle charge complex according to an exemplary embodiment of the present invention.

Referring to FIG. 2, when the complex 10 in which the metal nanoparticle 11 is linked with the photosensitizer 15 by the linker 12 is exposed to light having a wavelength capable of exciting the photosensitizer 15, energy transfer to the surface of the metal nanoparticle 11 from the photosensitizer 15 in the singlet excited state, that is, resonance energy transfer, may occur. In this case, the metal nanoparticle 11 may serve as a quencher to inhibit fluorescence of the photosensitizer 15 and production of a reactive oxygen species. As a result, the complex 10 may not have cytotoxicity.

During circulation of the complex 10 administered to the body in the blood, the photosensitizer 15 may not be dissociated from the metal nanoparticle 11 so that the complex 10 can be maintained. It is difficult for the complex 10 to penetrate a normal tissue having a relatively tight wall of the blood vessel because it is larger in size than the photosensitizer 15 itself. As a result, duration of the side effect of photosensitivity can be reduced.

However, the complex 10 may selectively penetrate the leaky wall of the newly-formed blood vessel present in the tumor to permeate a tumor tissue. Moreover, because of a difficulty in excretion through a lymphatic duct of the tumor, the complex 10 may be accumulated in the tumor, and stay longer. The complex 10 may be almost electrically neutral since components having opposite charges are bound to each other by the charge interaction. Thus, the complex 10 may very easily enter into tumor cells by the endocytosis, compared to the negatively or positively charged photosensitizer. As a result, the complex 10 can be specifically accumulated in the tumor tissue.

Referring to FIG. 3, in the complex 10 specifically accumulated in the tumor tissue, the photosensitizer 15 is slowly dissociated from the metal nanoparticle 11 according to time. Here, a distance between the photosensitizer 15 and the metal nanoparticle 11 exceeds a distance incapable of being quenched, for example, 20 nm. Afterwards, when the complex 10 is exposed to light having a wavelength capable of exciting the photosensitizer 15, the photosensitizer 15 is excited to a singlet energy state. Majority of the photosensitizers in the singlet excited state transit to a triplet excited state through intersystem crossing, and others return to a ground energy state by emitting energy in the form of fluorescence. The singlet or triplet-state photosensitizer produces a reactive oxygen species such as singlet oxygen, oxygen radical, super oxide, or peroxide by reaction with a surrounding substrate or oxygen. The produced reactive oxygen species may lead to apoptosis or necrosis of surrounding tumor cells.

The complex 10 specifically accumulated in the tumor tissue is slowly dissociated, and thus may effectively destroy the tumor tissue through the photodynamic therapy. In addition, the selective fluorescence in the tumor tissue may lead to a further improvement in accuracy of tumor diagnosis using the complex.

Figure 4:
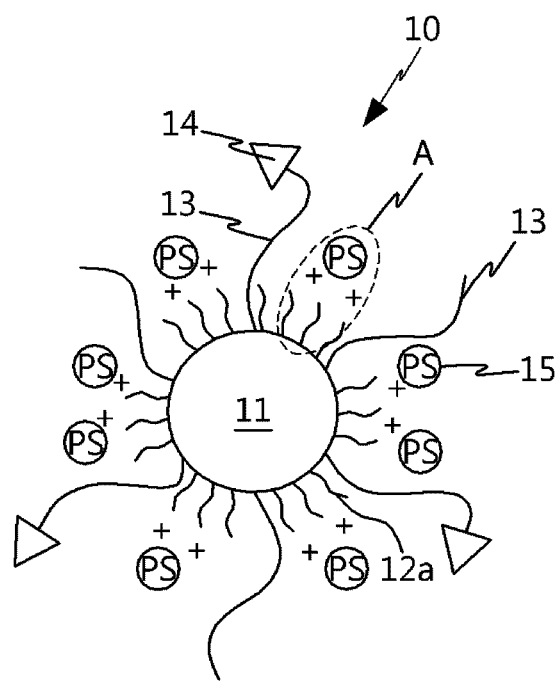
FIG. 4 is a schematic view of an example of the photosensitizer-metal nanoparticle charge complex of FIG. 1.
Figure 5:
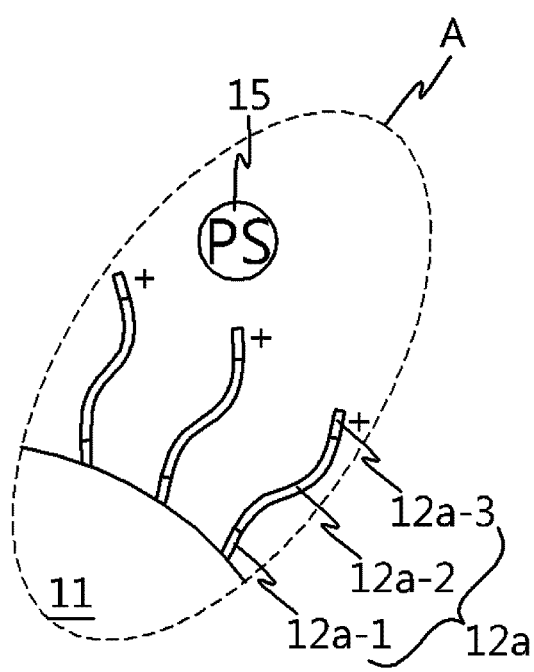
FIG. 5 is an enlarged schematic view of region A of FIG. 4.

FIG. 4 is a schematic view of an example of the photosensitizer-metal nanoparticle charge complex of FIG. 1, and FIG. 5 is an enlarged schematic view of region A of FIG. 4. A complex to be described in the exemplary embodiment is similar to that described with reference to FIG. 1 except for descriptions to be made below.

Referring to FIGS. 4 and 5, a linker 12a may be a polypeptide chemically bound to the metal nanoparticle 11 and capable of binding the photosensitizer 15 thereto by charge interaction.

As an example, the linker 12a may contain an amino acid having an anion or cation as a residue on one terminal (12a-3) thereof in a polar solvent and cysteine having a thiol group as a residue on the other terminal (12a-1). Thus, the linker 12a may be chemically adsorbed to a surface of the metal nanoparticle 11 by a metal-thiol bond and may bind the photosensitizer 15 thereto by charge interaction. An amino acid having a cation as a residue may be Arg, Lys or His, and an amino acid having an anion as a residue may be Asp or Glu. In a middle portion (12a-2) between the terminal (12a-3) and the other terminal (12a-1) of the linker 12a, an amino acid having a neutral alkyl group as a residue may be included. As a result, a plurality of linkers 12a, which are adjacent to each other, may be easily self-assembled and packed by van der Waals interaction. An example of the linker 12a may be Arg-Arg-Leu-Ala-Cys (RRLAC; SEQ ID NO: 1).

A hydrophilic polymer 13 may be chemically bound to the metal nanoparticle 11. Here, a terminal of the hydrophilic polymer 13 may contain a thiol group.

Figure 6:
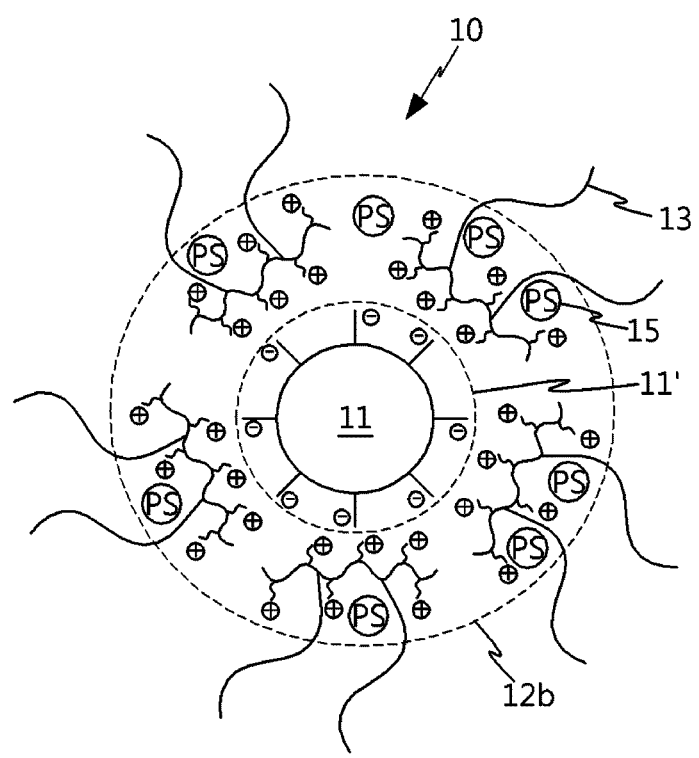
FIG. 6 is a schematic view of another example of the photosensitizer-metal nanoparticle charge complex of FIG. 1.

FIG. 6 is a schematic view of another example of the photosensitizer-metal nanoparticle charge complex of FIG. 1. A complex to be described in the exemplary embodiment is similar to that described with reference to FIG. 1 except for descriptions to be made below.

Referring to FIG. 6, a linker 12b may be a polypeptide or biocompatible polymer which is capable of being bound to both a metal nanoparticle 11 and a photosensitizer 15 by charge interaction.

As an example, the linker 12b may include Arg, Lys or His having a cation as a residue in a polar solvent, and Asp or Glu having an anion as a residue in a polar solvent. An example of the linker 12b may be poly(L-lysine) containing an amino group as a residue.

Another example of the linker 12b may be a biocompatible polymer having carboxylic acid or a salt thereof, sulfonic acid or a salt thereof, or an amine group as a substituent. Such a biocompatible polymer may be a polysaccharide; heparin or a derivative thereof; hyaluronic acid or a derivative thereof; gelatin or a derivative thereof; poly(acrylic acid) or a derivative thereof; polylysine or a derivative thereof; poly(ethylene imine) or a derivative thereof; chitosan or a derivative thereof; or polyvinylpyrrolidone or a derivative thereof, which has carboxylic acid or a salt thereof, or sulfonic acid or a salt thereof as a substituent.

The metal nanoparticle 11 may be directly bound to the linker 12b by charge interaction because of free movement of charges, which is a characteristic of a metal. However, to further facilitate the charge interaction between the linker 12b and the metal nanoparticle 11, a surface of the metal nanoparticle 11 may be modified. To this end, a modifying part 11' with a charge having an opposite polarity to that of the linker 12b may be coated on the surface of the metal nanoparticle 11. The modifying part 11' may be bound to the surface of the metal nanoparticle 11 by a metal-thiol bond, and include a carboxylate anion, a sulfonate anion or an ammonium cation on its terminal. An example of the modifying part 11' may be mercaptosuccinic acid (MSA). Here, an absolute value of a total charge amount of the linker 12b should be higher than that of the modifying part 11' to easily bind the photosensitizer 15.

Meanwhile, the hydrophilic polymer 13 may be bound to the linker 12b. An example of the linker 12b including the hydrophilic polymer 13 may be polyethylene glycol-graft-poly(L-lysine) (PEG-g-PLL).

Pharmaceutical Composition containing Photosensitizer-Metal Nanoparticle Charge Complex In still another exemplary embodiment of the present invention, a pharmaceutical composition containing the photosensitizer-metal nanoparticle charge complex described with reference to FIG. 1 is provided.

The pharmaceutical composition according to the exemplary embodiment includes a pharmaceutically effective amount of the photosensitizer-metal nanoparticle charge complex, and a pharmaceutically available carrier. The carrier may be a diluent. The composition may further include an additive, such as a preservative, a wetting agent, an emulsifier, or a dispersing agent.

Such a pharmaceutical composition may be formulated in accordance with a desired administration route. Examples of the administration route may include, but are not limited to, non-oral administrations, including intravenous, intradermal, subcutaneous, intranasal, percutaneous (local), transmucosal and rectal administrations.

Appropriate carriers used for non-oral administrations are well known to those skilled in the art. Examples of the carrier may include aqueous vehicles including, but not limited to, a sodium nitride injection, a Ringer's solution, a dextrose injection, an injection containing dextrose and sodium nitride, and a lactate Ringer's solution; water-miscible vehicles including, but not limited to, ethyl alcohol, PEG, and polypropylene glycol; and non-aqueous vehicles including, but not limited to, corn oil, cottonseed oil, peanut oil, sesame oil, ethyl oleate, isopropyl myristate, and benzyl benzoate.

Such a pharmaceutical composition may be used to treat or diagnose a tumor. When used to treat or diagnose a tumor, an effective amount may be determined by a physician depending on cases. Here, a patient's age, sex, body weight, or severity of the disease to be treated or diagnosed may be considered. As one example, the photosensitizer-metal nanoparticle charge complex may be administered in an amount of 0.001 μg to 10 mg per kilogram based on an equivalent weight of the photosensitizer and the body weight of the patient. In a specific example, the complex may be administered in an amount of 0.1 to 5 mg/kg.

EXAMPLES

Hereinafter, exemplary examples will be disclosed to help understanding of the present invention. However, the exemplary examples are merely to explain the present invention, and not to limit the scope of the present invention.

Preparation Example 1

Preparation of Photosensitizer-Metal Nanoparticle Charge Complex (I)

Preparation Example 1-1

Preparation of Metal Nanoparticle (MSA-GNP) whose Surface is charged with Negative Charge 100 ml of 0.01 wt/v % $HAuCl_4$ solution was heated for 10 minutes, and 3 ml of 1wt/v % sodium citrate was added thereto. As a color of the resulting solution was changed from yellow to purple after additional 20-minute heating, a gold nanoparticle (GNP) colloid (citrate-GNP) which was electrostatically coated with citrate, and capable of stably maintaining an anionic surface state, was obtained. Afterwards, 8 ml of 1 wt/v % mercaptosuccinic acid (MSA) aqueous solution was added to 60 ml of GNP colloid (citrate-GNP) at 50° C. to react for 12 hours, thereby obtaining an MSA-GNP solution in which MSA was chemically adsorbed to a GNP surface. The MSA-GNP solution was added to a dialysis membrane (MWCO=50000) for dialysis in distilled water, thereby removing MSA and citrate which did not participate in the reaction.

Preparation Example 1-2

Synthesis of PEG-g-PLL 100 mg of poly-L-lysine hydrobromide (PLL-HBr; Mw=30000~70000 Da) was dissolved in 3 ml of 50 mM sodium tetraborate buffer (pH 8.5), and 250 mg of methoxy polyethyleneglycol succinimidyl glutarate (mPEG-SG; Mw=5000 Da) was added thereto to react for 6 hours at room temperature. To remove mPEG-SG which did not participate in the reaction, an aqueous solution was obtained through dialysis for 48 hours using a dialysis membrane (MWCO=10000). The aqueous solution was freeze-dried, thereby obtaining a resulting product. The product was analyzed using 600 MHz $^1$H-NMR spectrometer, and as a result, it was confirmed that PEG-g-PLL(EGL) in which PEG was bound to 14% of residues of PLL was synthesized.

Preparation Example 1-3a

Synthesis of Photosensitizer-Gold Nanoparticle Charge Complex ($MSA-GNP/EGL/AlPcS_4$)

200 μl of the MSA-GNP aqueous solution obtained in Preparation Example 1-1 was mixed with 200 μl of the EGL aqueous solution having a concentration of 5.6 mg/ml, which was obtained in Preparation Example 1-2, and 10 mM phosphate buffer (pH 7.4) was added thereto to make a total volume of 1 ml. Afterwards, the resulting product was maintained at room temperature for 30 minutes, thereby obtaining an MSA-GNP/EGL complex. Here, 5 μl of an Al(III) phthalocyanine chloride tetrasulfonic acid ($AlPcS_4$) aqueous solution having a concentration of 36 mg/ml was added, and maintained at room temperature for 30 minutes, thereby preparing a photosensitizer-gold nanoparticle charge complex, that is, an $MSA-GNP/EGL/AlPcS_4$ complex.

Preparation 1-3b

Synthesis of Photosensitizer-Gold Nanoparticle Charge Complex ($MSA-GNP/EGL/AlPcS_4$)

An MSA-GNP/EGL complex and an $MSA-GNP/EGL/AlPcS_4$ complex were prepared by the same method as described in Preparation Example 1-3a except for using 400 μl of the MSA-GNP aqueous solution obtained in Preparation Example 1-1.

Analysis Example 1

Analyses of Hydrohynamic Volume Distribution and Surface Zeta Potential of Particles Distribution of hydrodynamic sizes and surface zeta potentials of particles were measured through dynamic light scattering.

The MSA-GNP obtained in Preparation Example 1-1 had a hydrodynamic size of 35.8±2.2 nm and a surface zeta potential of −27.3±0.1 mV.

A hydrodynamic size of the MSA-GNP/EGL complex obtained during Preparation Example 1-3a was 110.4±12.5 nm, and a surface zeta potential thereof was 3.4±0.4 mV. In addition, a hydrodynamic size of the $MSA-GNP/EGL/AlPcS_4$ complex prepared as a resulting product of Preparation Example 1-3a was 55 nm, and a surface zeta potential thereof was 2.25 mV. Here, it is estimated that the reason why the value of the surface zeta potential was lower than expected is that the PEG contained in the EGL is distributed on the outermost surface of the nanoparticle, thereby reducing an average of the zeta potential values.

A hydrodynamic size of the MSA-GNP/EGL complex obtained during Preparation Example 1-3b was 151.05±52.3 nm, and a surface zeta potential thereof was 3.35±1.7 mV. A hydrodynamic size of the MSA-GNP/EGL/AlPcS$_4$ complex prepared as a resulting product of Preparation Example 1-3b was 61 nm, and the surface zeta potential thereof was 4.7 mV.

Figure 7:
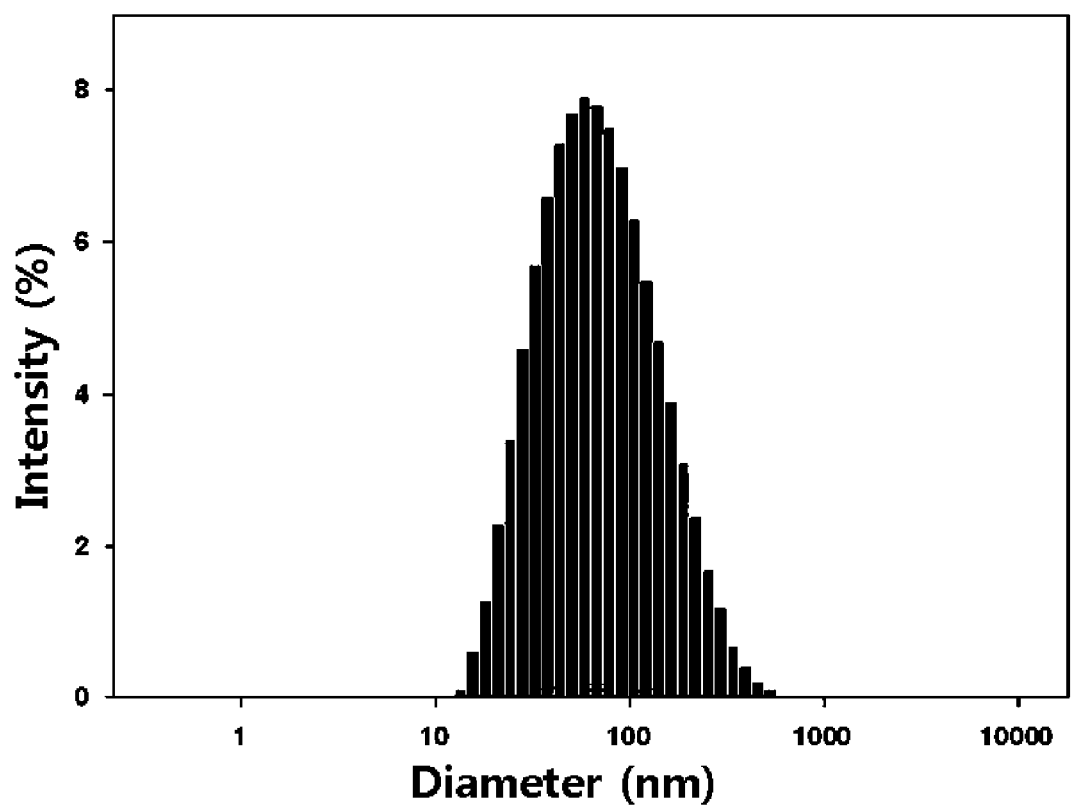
FIG. 7 is a graph showing size distribution of an MSA-GNP/EGL/AlPcS$_4$ complex prepared as a product according to Preparation Example 1-3b.

FIG. 7 is a graph showing distribution of hydrodynamic size of the MSA-GNP/EGL/AlPcS$_4$ complex prepared as the resulting product of Preparation Example 1-3b, and referring to FIG. 7, it can be seen that an average size of the MSA-GNP/EGL/AlPcS$_4$ complex prepared as the resulting product of Preparation Example 1-3b was 61 nm.

It can be seen that, compared to the MSA-GNP/EGL complexes in Preparation Examples 1-3a and 1-3b, the hydrodynamic size of the MSA-GNP/EGL/AlPcS$_4$ complex was significantly decreased, which may be because AlPcS$_4$ charged with a negative charge was added to the MSA-GNP/EGL complex charged with a positive charge, and thus the EGL layer became denser. Thus, it can be seen that a more compact and stable charge complex is prepared by adding AlPcS$_4$.

Figure 8:
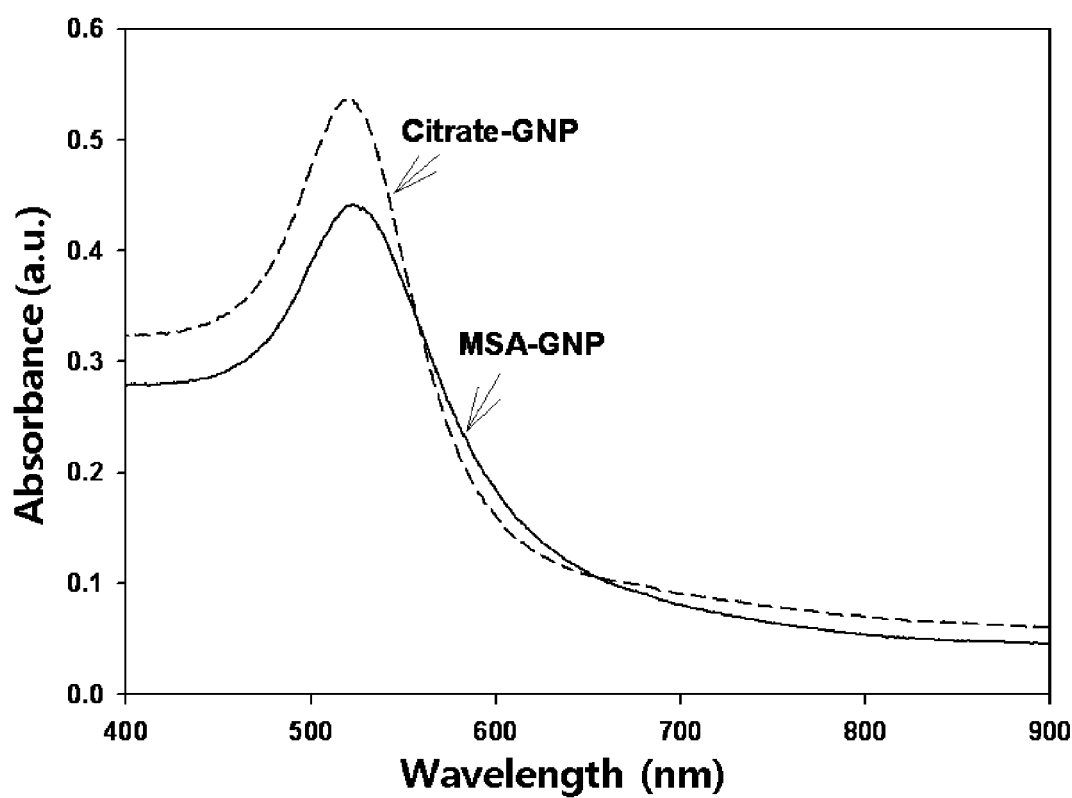
FIG. 8 is a graph showing UV/Vis absorption spectrums of citrate-GNP and MSA-GNP prepared according to Preparation Example 1-1.

FIG. 8 is a graph showing UV/Vis absorption spectrums of citrate-GNP and MSA-GNP prepared in Preparation Example 1-1.

Referring to FIG. 8, both the citrate-GNP and MSA-GNP had typical absorption peaks at 530 nm, and similar UV/Vis absorption spectrums.

Figure 9:
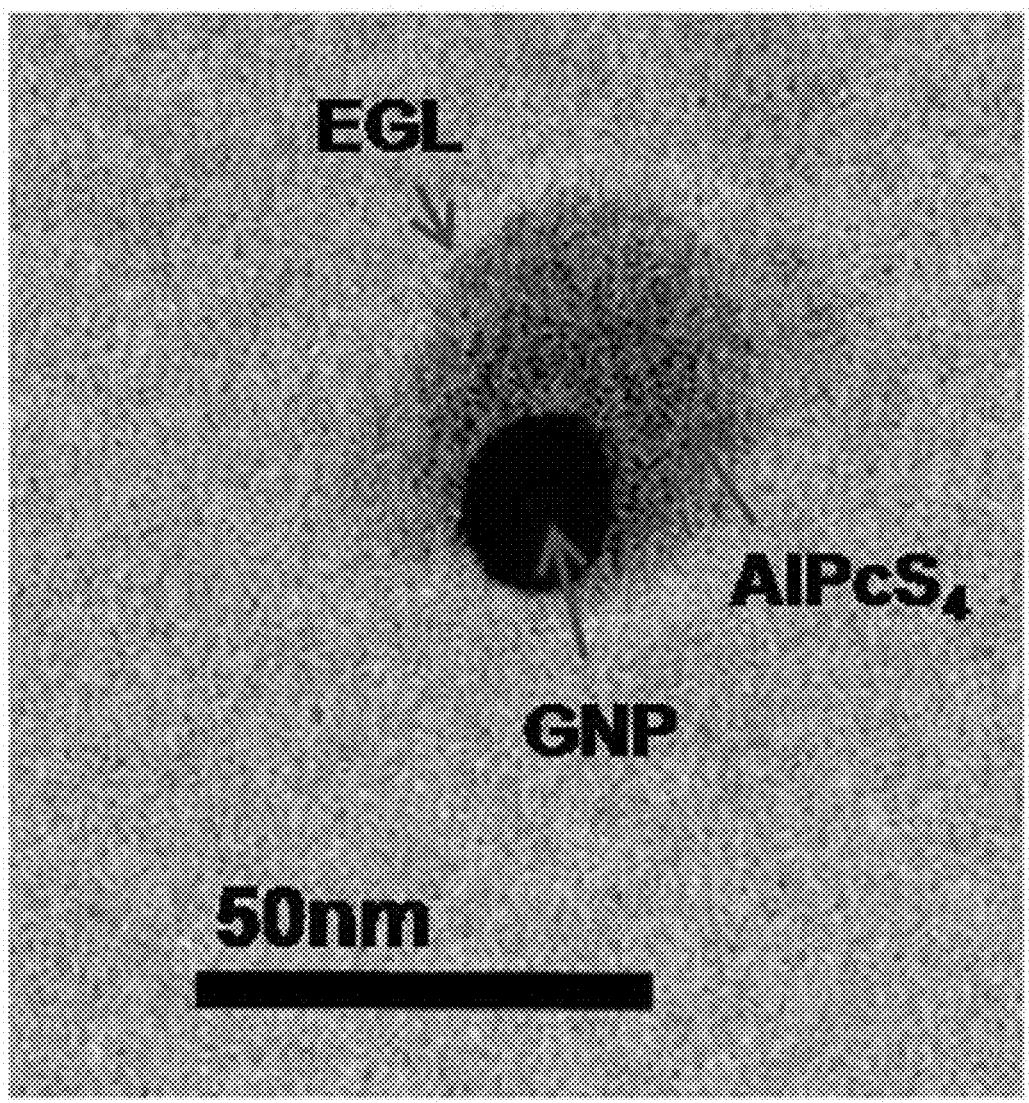
FIG. 9 is a transmission electron microscope (TEM) photograph of the MSA-GNP/EGL/AlPcS$_4$ complex prepared as the product according to Preparation Examples 1-3b.

FIG. 9 is a transmission electron microscope (TEM) photograph of the MSA-GNP/EGL/AlPcS$_4$ complex prepared as the resulting product in Preparation Examples 1-3b.

Referring to FIG. 9, it can be confirmed that the EGL layer was coated on MSA-GNP, and AlPcS$_4$ was disposed in the EGL layer. Here, due to carboxylate (—COO$^-$) having a negative charge in the MSA and primary ammonium (—NH$_3^+$) having a positive charge, which is a residue of the EGL, the EGL layer may be coated on the MSA-GNP by electrostatic attraction.

Analysis Example 2

Analyses of Stability and Fluorescence of MSA-GNP/EGL/AlPcS$_4$ Complex

The MSA-GNP/EGL/AlPcS$_4$ complexes prepared in Preparation Examples 1-3a and 1-3b and AlPcS$_4$ were dissolved in phosphate buffered saline (PBS; 6.7 mM, pH 7.4, NaCl 154 mM) at equivalent concentrations, and exposed to light at 660 nm for excitation. Afterwards, fluorescence values were measured at 690 nm in 10-minute intervals for 3 hours.

Figure 10:
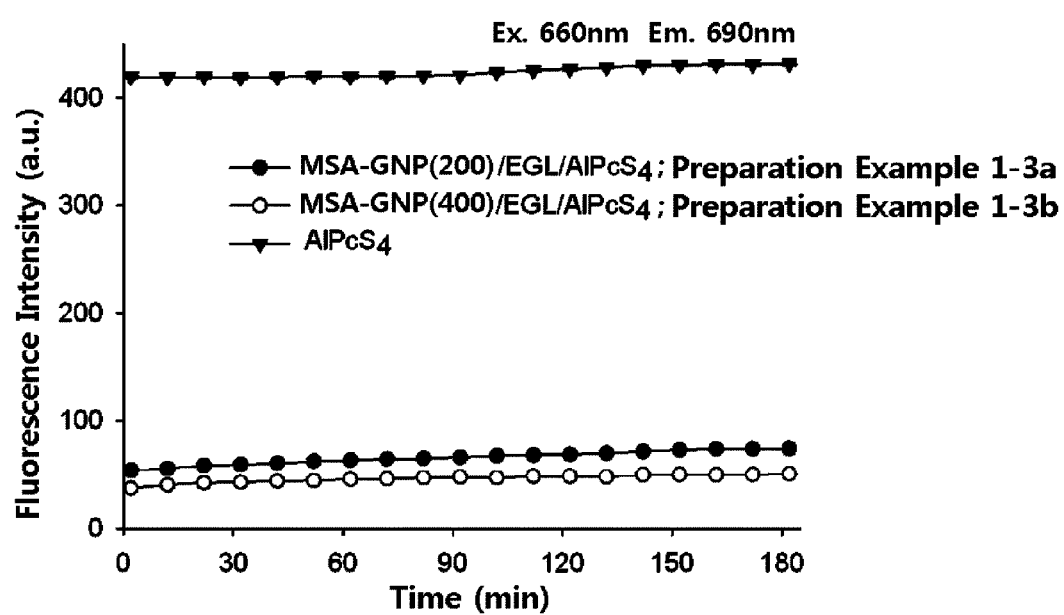
FIG. 10 is a graph showing fluorescence intensities of the MSA-GNP/EGL/AlPcS$_4$ complexes and AlPcS$_4$ according to time after excitement with light.

FIG. 10 is a graph showing fluorescence intensities of the MSA-GNP/EGL/AlPcS$_4$ complexes and AlPcS$_4$, which are excited by light, according to time.

Referring to FIG. 10, the MSA-GNP/EGL/AlPcS$_4$ complexes exhibited lower fluorescence intensities, i.e., about ⅛ level of the AlPcS$_4$ compared to the AlPcS$_4$ having the same concentration. This shows that florescence was quenched because of the preparation of the MSA-GNP/EGL/AlPcS$_4$ complexes. The steady fluorescence values of the MSA-GNP/EGL/AlPcS$_4$ complexes were maintained for 3 hours, which indicates that the complex itself was stably maintained.

One equivalent weight of each of the MSA-GNP/EGL/AlPcS$_4$ complexes prepared in Preparation Examples 1-3a and 1-3b and AlPcS$_4$ was dissolved in PBS (6.7 mM, pH 7.4, NaCl 154 mM). Some groups were photographed in white light, and the others were photographed by being irradiated with light at 365 mm.

Figure 11:
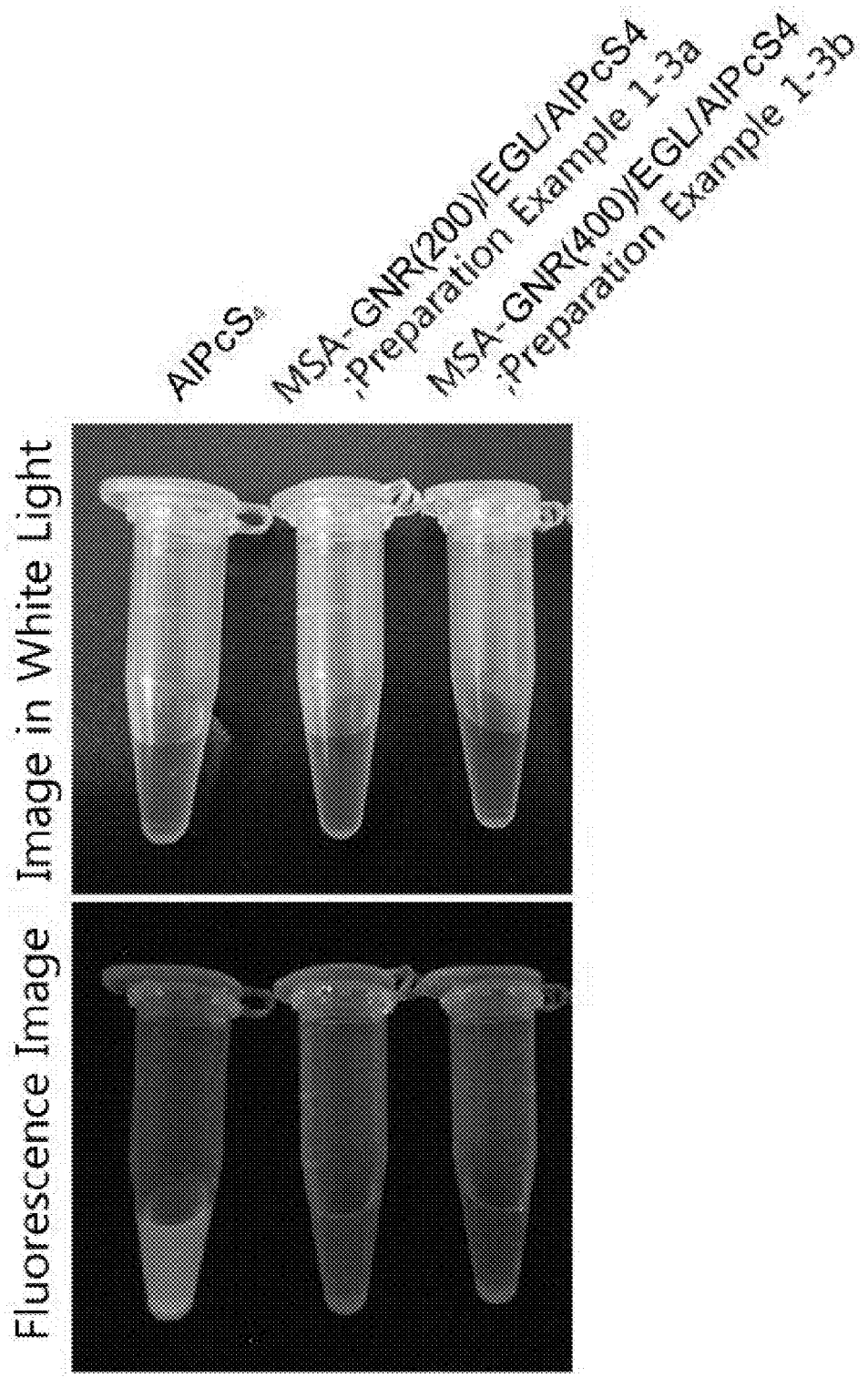
FIG. 11 shows photographs of images and fluorescence images of the MSA-GNP/EGL/AlPcS$_4$ complexes and AlPcS$_4$, which are taken in white light and in light at 365 nm.

FIG. 11 shows photographs of images, which are taken in white light, and fluorescent images, which are taken in light at 365 nm, of the MSA-GNP/EGL/AlPcS$_4$ complexes and AlPcS$_4$, respectively.

Referring to FIG. 11, it can be seen that, after irradiation with light at 365 nm, the AlPcS$_4$ emitted fluorescence, but the emission of fluorescence was inhibited in the MSA-GNP/EGL/AlPcS$_4$ complexes.

Preparation Example 2

Preparation of Photosensitizer-Gold Nanoparticle Charge Complex (II)

Preparation Example 2-1

Preparation of Gold Nanorod (GNR)

A gold nanorod was prepared by a seed-mediated method. Specifically, 7.5 ml of a cetyltrimethylammonium bromide (CTAB) aqueous solution, which was prepared by dissolving CTAB in tertiary distilled water to have a molarity of 100 mM, was mixed with 250 µl of a 10 mM HAuCl$_4$ aqueous solution (HAuCl$_4$.3H$_2$O), followed by adding 600 µl of an aqueous solution prepared by dissolving 10 mM NaBH$_4$ in tertiary distilled water thereto. The resulting solution was stirred for 2 minutes, and maintained at 25° C. for 2 hours, thereby preparing a seed solution.

Meanwhile, 1.7 ml of a 10 mM HAuCl$_4$ aqueous solution (HAuCl$_4$.3H$_2$O) was added to 40 ml of a 100 mM CTAB aqueous solution, followed by sequentially adding 250 µl of a 10 mM AgNO$_3$ aqueous solution prepared by dissolving AgNO$_3$ in tertiary distilled water and 270 µl of a 100 mM ascorbic acid aqueous solution prepared by dissolving ascorbic acid in tertiary distilled water. Here, 420 µl of the seed solution was added to react for 12 hours, and centrifuged with 15000 g at 25° C. for 15 minutes, thereby obtaining the gold nanorod (GNR). A surface zeta potential of the gold nanorod coated with CTAB was measured as 65.8 mV.

Figure 12:
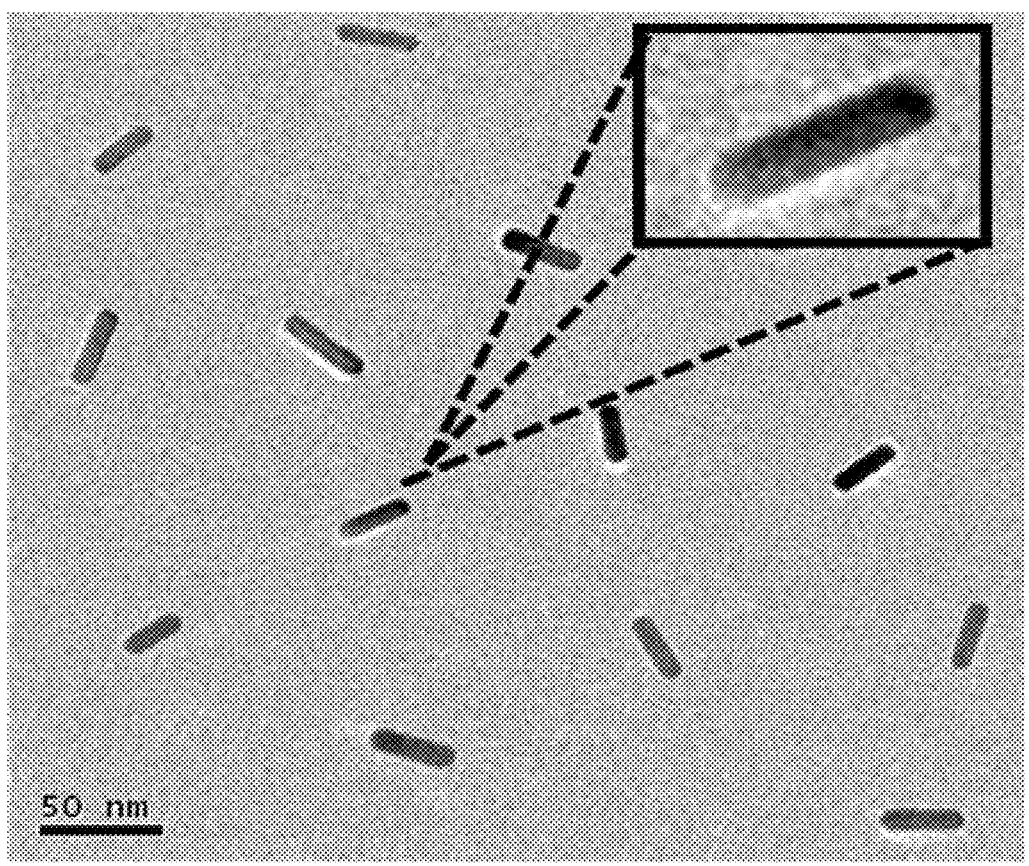
FIG. 12 is a TEM photograph of a gold nanorod (GNR) prepared according to Preparation Example 2-1.

FIG. 12 is a TEM photograph of the gold nanorod (GNR) prepared according to Preparation Example 2-1.

Referring to FIG. 12, it can be seen that the gold nanorod having an average length of 34 nm and a width of 9 nm was formed.

Preparation Example 2-2

Synthesis of RRLAC (Arg-Arg-Leu-Ala-Cys)

RRLAC (Arg-Arg-Leu-Ala-Cys) was synthesized by coupling amino acids one by one from a C-terminal using a general fluorenylmethoxycarbonyl solid phase peptide synthesis (Fmoc SPPS) method. Reagents used herein were NH$_2$-Cys(Trt)-2-chloro-trityl resin, Fmoc-Leu-OH, Fmoc-Ala-OH, and Fmoc-Arg(Pbf)-OH, and as coupling agents, HBTU (O-(Benzotriazol-1-yl)-N,N,N',N'-tetramethyluronium hexafluorophosphate), HOBt(Hydroxybenzotriazole), and NMM were used. Fmoc was removed with a 20% piperidine dimethylformamide (DMF) solution. To isolate a synthesized peptide from the resin and deprotect a residue, a mixture of trifluoroacetic acid (TFA), 1,2-ethanedithiol (EDT), thioanisole, triisopropylsilane (TIS) and water in a volume ratio of 90:2.5:2.5:2.5:2.5 was used. First, the coupling agents, that is, HBTU (8 equivalent weights), HOBt (8 equivalent weights), and NMM (16 equivalent weights) were dissolved in DMF, and then added to an amino acid (8 equivalent weights) in which an amino group was protected with Fmoc and whose residue was protected. Afterwards, a coupling reaction was performed on the resulting solution at room temperature for 2 hours. For Fmoc deprotection, a 20% piperidine DMF solution was added to react at room temperature twice each for 5 minutes. By repeating the coupling reaction and Fmoc-deprotection, a peptide backbone was formed, and then treated with the mixture of TFA, EDT, thioanisole, TIS, and water in the volume ratio of 90:2.5:2.5:2.5:2.5 to isolate the peptide from the resin. The isolated peptide was purified by high performance liquid chromatography (HPLC), assayed by mass spectroscopy, and freeze-dried to obtain a final peptide product. The synthesized peptide was confirmed as the peptide having a RRLAC sequence and a molecular weight of 618 g/mol by MALDI-TOF mass analysis.

Preparation Example 2-3

Preparation of RRLAC-GNR-PEG whose Surface is Charged with Positive Charge

The gold nanorod prepared in Preparation Example 2-1 was dispersed in tertiary distilled water to prepare 500 μl of a gold nanorod aqueous solution (4 nM), and mixed with 50 μl of an mPEG-SH aqueous solution (1 mM) prepared by dissolving thiol-terminated methoxy polyethyleneglycol (PEG) (mPEG-SH, molecular weight: 5000) in tertiary distilled water to react at 25° C. for 20 hours, thereby obtaining a pegylated gold nanorod (GNR-PEG). Remaining mPEG-SH which did not participate in the reaction was centrifuged with 15000 g at 25 r for 15 minutes to be removed, and the pegylated gold nanorod was redispersed in phosphate buffer (10 mM, pH 7.4), thereby preparing a pegylated gold nanorod (GNR-PEG) solution. A zeta potential of the pegylated gold nanorod was measured as −26.4 mV.

The RRLAC peptide prepared in Preparation Example 2-2 was dissolved in tertiary distilled water to prepare 100 μl of a 2 mM RRLAC peptide aqueous solution, and mixed with 900 μl of the pegylated gold nanorod (GNR-PEG) solution to react at 25° C. for 12 hours. Remaining peptides which did not participate in the reaction were removed by centrifugation, and the resulting product was redispersed in tertiary distilled water, thereby obtaining a pegylated gold nanorod (RRLAC-GNR-PEG) aqueous solution in which the RRLAC peptide was conjugated to its surface and charged with a positive charge. A surface zeta potential of the RRLAC-GNP-PEG was measured as +21.7 mV, which indicates that the surface of the particle was charged with a positive charge.

Preparation Example 2-4

Synthesis of Photosensitizer-Gold Nanoparticle Charge Complex (GNR/AlPcS$_4$ Complex, RRLAC-GNR-PEG/AlPcS$_4$)

50 μl of a 4 mM AlPcS$_4$ aqueous solution prepared by dissolving AlPcS$_4$ in tertiary distilled water was mixed with 950 μl of the 4 nM RRLAC-GNP-PEG aqueous solution obtained in Preparation Example 2-3 to react at 25° C. for 1 hour. Free AlPcS$_4$ which did not form complex with RRLAC-GNP-PEG was removed by passing the resulting solution through a PD-10 desalting column (GE Healthcare) to obtain a photosensitizer-gold nanorod charge complex, RRLAC-GNR-PEG/AlPcS$_4$, in which AlPcS$_4$ was bound to the RRLAC-GNR-PEG by charge-charge interaction, i.e., a GNR/AlPcS$_4$ complex. As an effluent of the column, tertiary distilled water was used. A surface zeta potential of the RRLAC-GNR-PEG/AlPcS$_4$ was measured as −4.7 mV, which indicates that AlPcS$_4$ charged with a negative charge was bound to the positively charged peptide by charge-charge interaction, and thus a charge at the surface of the particle of the complex was changed from positive to negative.

Figure 13:
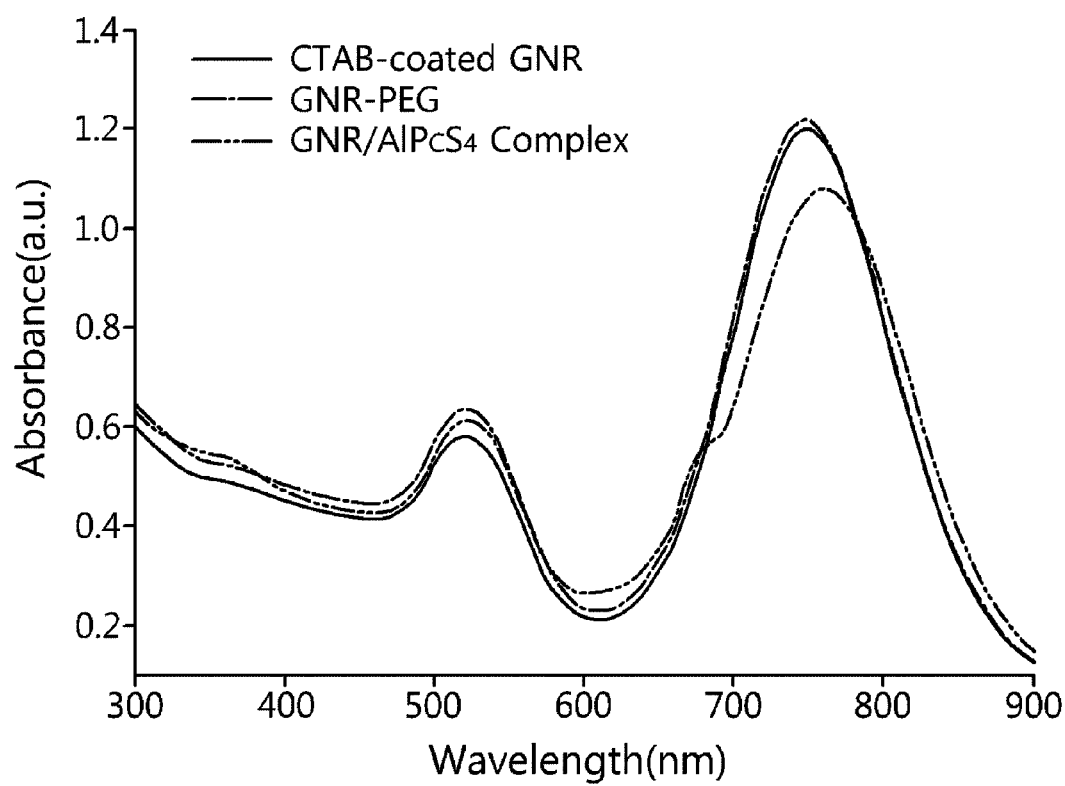
FIG. 13 is a graph showing absorption, according to wavelength, of a CTAB-coated GNR according to Preparation Example 2-1, a GNR-PEG according to Preparation Example 2-3, and a GNR-AlPcS$_4$ complex according to Preparation Example 2-4.

FIG. 13 is a graph showing absorption, according to wavelength, of the CTAB-coated GNR according to Preparation Example 2-1, the GNR-PEG according to Preparation Example 2-3, and the GNR/AlPcS$_4$ complex according to Preparation Example 2-4. Here, the absorption was measured using a UV/Vis scanning spectrophotometer (DU730, Beckman).

Referring to FIG. 13, the CTAB-coated GNR has molar absorption coefficients of $1.3×10^9$ M$^{-1}$ cm$^{-1}$ and $4.6×10^9$ M$^{-1}$ cm$^{-1}$ at 510 nm and 785 nm, respectively. Meanwhile, AlPcS$_4$ was known to have a molar absorption coefficient of $1.7×10^5$ M$^{-1}$ cm$^{-1}$ at 675 nm. By calculating using these values, in the GNR/AlPcS4 complex, the AlPcS$_4$ was bound with the GNR in an average molar ratio of 1:2500.

Analysis Example 2-1

Analyses of Fluorescence and Efficiency of Generation of Singlet Oxygen from GNR/AlPcS$_4$ Complex To observe a fluorescence inhibitory characteristic, the GNR/AlPcS$_4$ complex and AlPcS$_4$ was dissolved in PBS (6.7 mM, pH 7.4, NaCl 154 mM), and their fluorescence values were measured (Ex. 660 nm, Em. 690 nm). Here, 10 μM AlPcS$_4$ equivalent was included in each solution.

Figure 14:
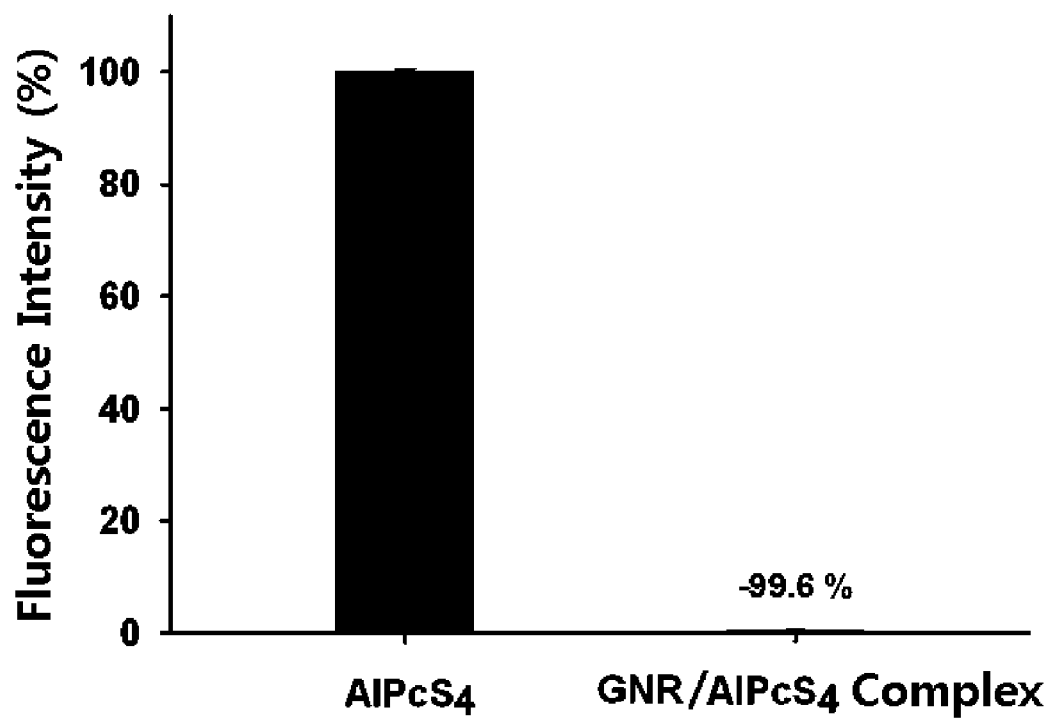
FIG. 14 is a graph showing fluorescence intensities of the AlPcS$_4$ and GNR-AlPcS$_4$ complex.

FIG. 14 is a graph showing fluorescence intensities of the AlPcS$_4$ and GNR/AlPcS$_4$ complex.

Referring to FIG. 14, the GNR/AlPcS$_4$ complex has a fluorescence intensity corresponding to 0.4% based on AlPcS$_4$. It seems that when AlPcS$_4$ was adjacent to a surface of the GNR in the GNR/AlPcS$_4$ complex, the production of the fluorescence signal was inhibited.

To observe an inhibitory characteristic with respect to singlet oxygen generation, each of AlPcS$_4$ and GNR/AlPcS$_4$ complex, and a singlet oxygen detecting reagent (singlet oxygen sensor green, Molecular probes) were dissolved in PBS (6.7 mM, pH 7.4, NaCl 154 mM) to make AlPcS$_4$ solution and GNR/AlPcS$_4$ complex solution. Each solution was irradiated with laser at 670 nm (irradiation dose: 0.79 J/cm$^2$, irradiation power: 26.3 mW/cm$^2$). Afterwards, fluorescence of the singlet oxygen detecting reagent (Ex./Em.: 504 nm/525 nm) was measured to compare efficiencies of production of singlet oxygen in two solutions.

Figure 15:
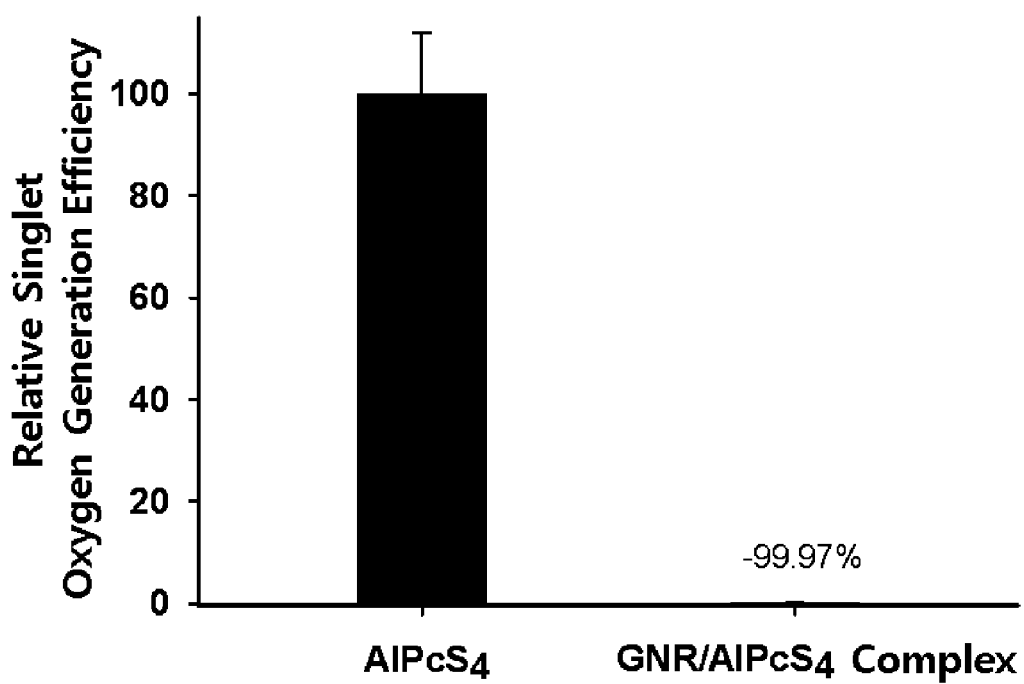
FIG. 15 is a graph showing relative generation efficiency of singlet oxygen in the AlPcS$_4$ and GNR-AlPcS$_4$ complex.

FIG. 15 is a graph showing efficiencies of generation of singlet oxygen in the AlPcS$_4$ and GNR-AlPcS$_4$ complex.

Referring to FIG. 15, the GNR/AlPcS$_4$ complex shows the efficiency of generation of the singlet oxygen corresponding to 0.03% based on AlPcS$_4$. It seems that, in GNR/AlPcS$_4$ complex, AlPcS$_4$ was adjacent to the surface of the GNR, thereby inhibiting generation of the singlet oxygen.

Analysis Example 2-2

Analysis of Release Rate of AlPcS$_4$ from GNR/AlPcS$_4$ Complex

D-Tube™ (Dialyzer Maxi, MWCO: 12-14 kDa, Novagen) was filled with the GNR/AlPcS$_4$ complex solution according to Preparation Example 2-4, immersed in 200 ml of PBS (6.7 mM, pH 7.4, NaCl 154 mM) solution, and gently shaken at 37° C. to release AlPcS$_4$ from the GNR/AlPcS$_4$ complex out of the tube. The PBS solution outside the tube was taken at intervals of 30 minutes, and then fluorescence (Ex. 660 nm, Em. 690 nm) of the collected solution was measured each time. The released amount of AlPcS$_4$ from the GNR/AlPcS$_4$ complex was calculated by comparing with a fluorescence calibration curve of an AlPcS$_4$ standard aqueous solution whose concentration has already been known.

Figure 16:
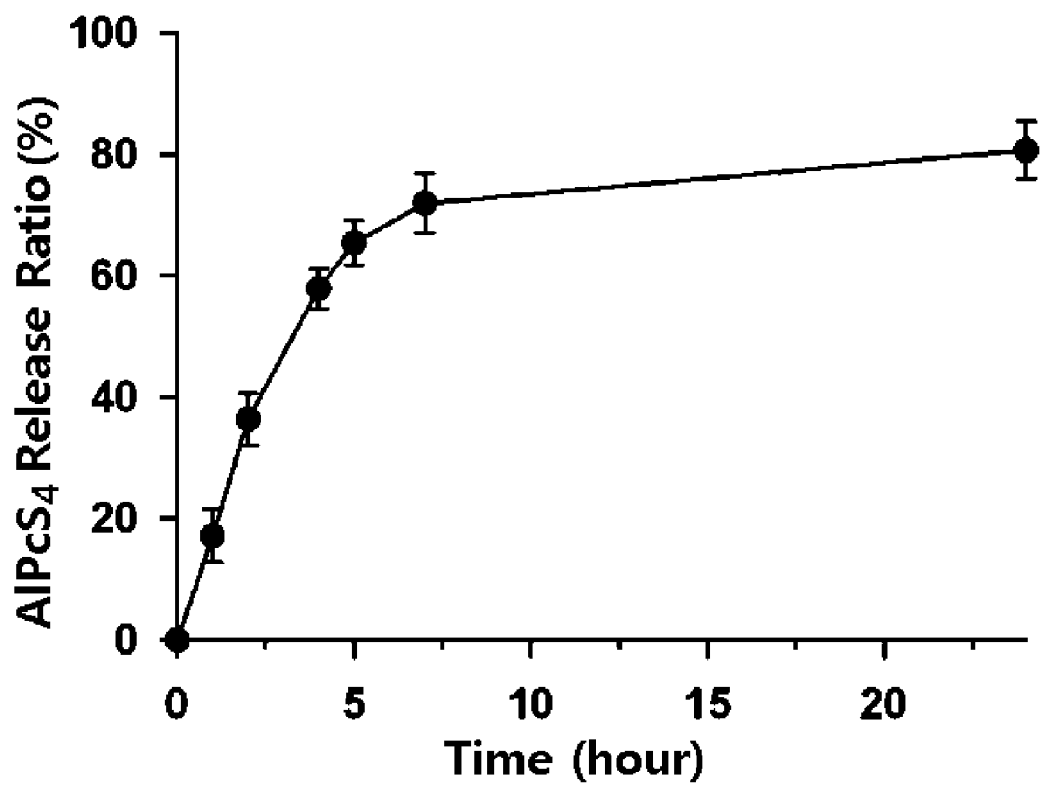
FIG. 16 is a graph showing a release rate of the AlPcS$_4$ according to time.

FIG. 16 is a graph showing a release rate of the AlPcS$_4$ according to time.

Referring to FIG. 16, it can be seen that the AlPcS$_4$ bound onto GNR by charge-charge interaction was slowly released for 24 hours, about 60% of a total amount of bound AlPcS$_4$ was released within 5 hours, and the remainder still constituted the complex with GNR.

Analysis Example 2-3

Analysis of Uptake of GNR/AlPcS$_4$ complex into Cell 90000 cells of a SCC7 (Squamous cell Carcinoma) cell line per well were seeded in a cell culture container (LebTek II Chambered coverglass), and cultured for 24 hours. Afterwards, each of the AlPcS$_4$ and GNR/AlPcS$_4$ complex according to Preparation Example 2-4 was diluted with a cell culture medium to have an equivalent concentration of 5 µM AlPcS$_4$. 600 µl of the diluted solution per well was added, and maintained at 37° C. for 4 hours. Subsequently, after the cell culture medium containing the photosensitizer was removed, the cells were washed three times, and then filled with a fresh cell culture medium to observe fluorescence using a confocal microscope (Ex. 633 nm, Em. 636-721 nm).

Figure 17:
FIGS. 17 and 18 are photographs showing fluorescence emitted in SCC7 cell lines treated with the AlPcS$_4$ and GNR-AlPcS$_4$ complex, respectively.
Figure 18:
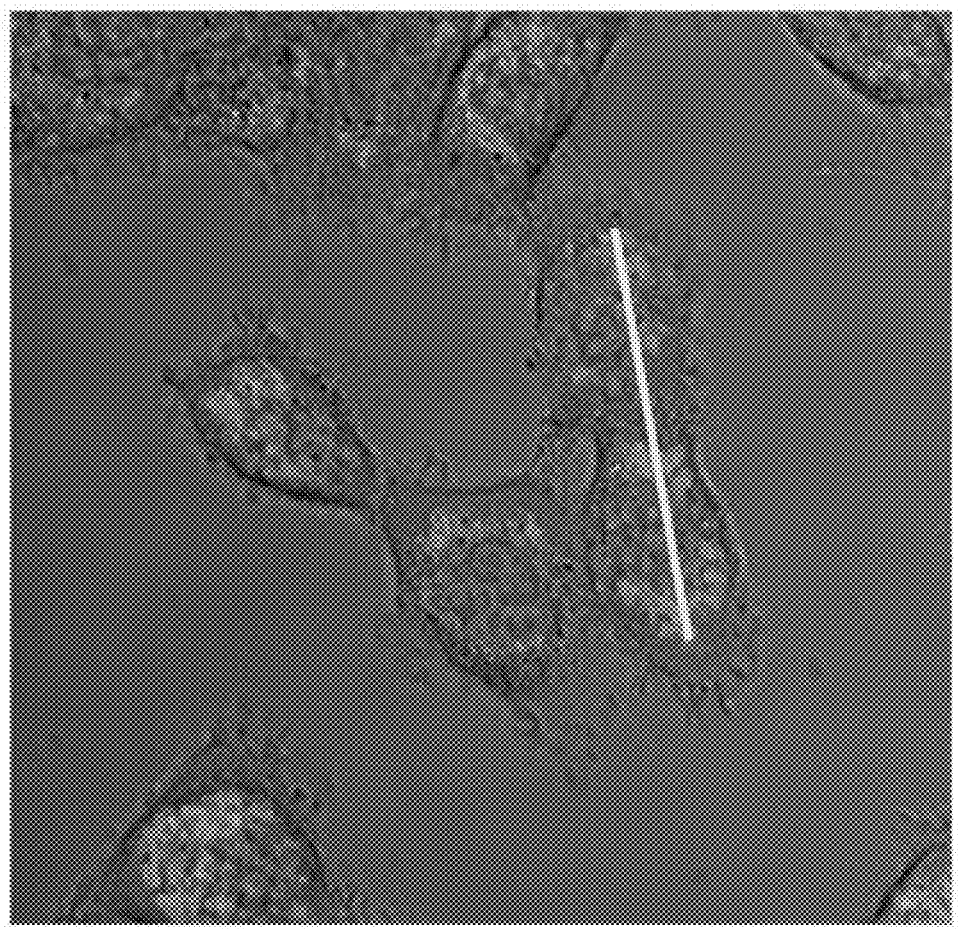
Figure 19:
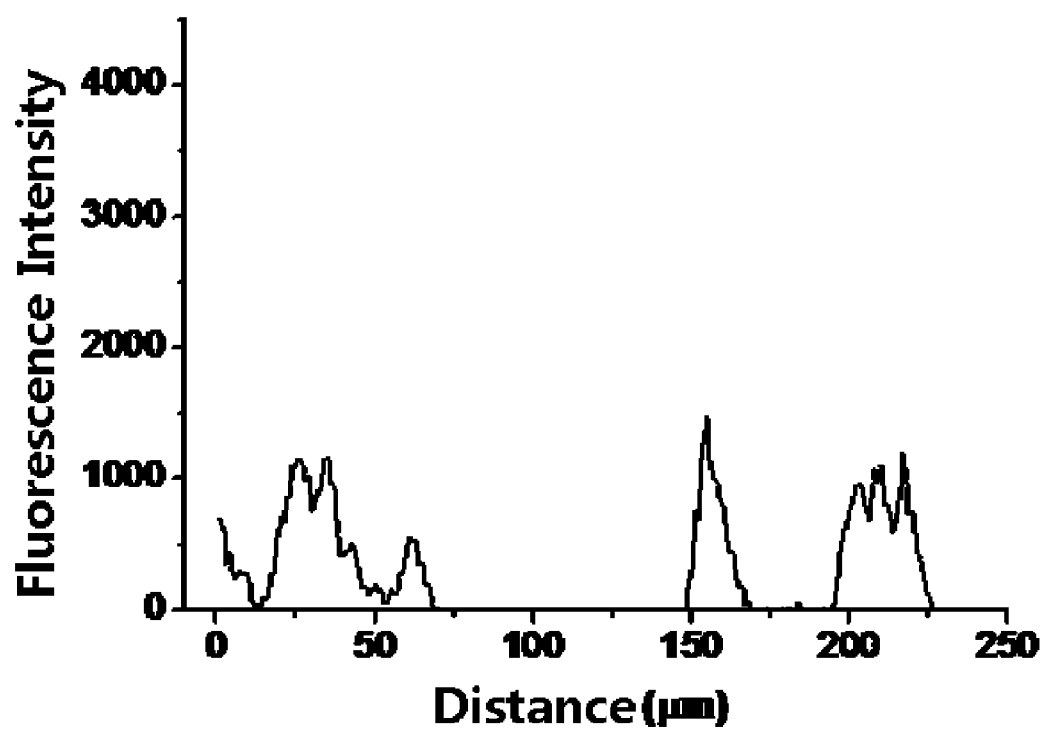
FIGS. 19 and 20 are graphs showing fluorescence intensities measured based on lines drawn in FIGS. 17 and 18, respectively.
Figure 20:
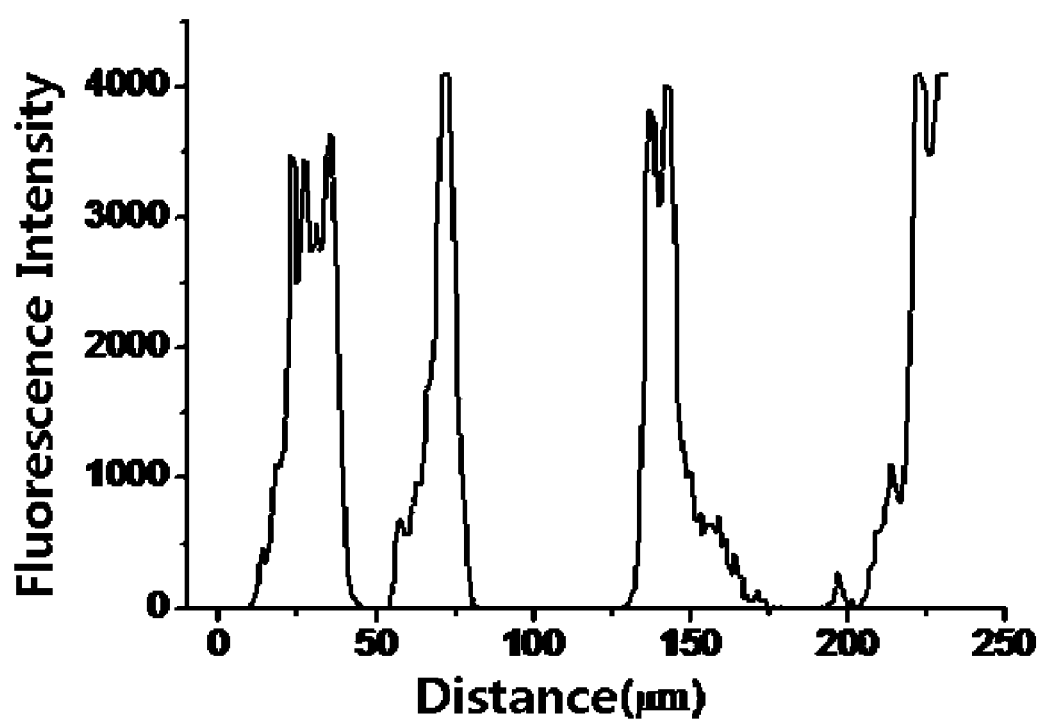

FIGS. 17 and 18 are photographs showing fluorescence shown in the SCC7 cell lines treated with the AlPcS$_4$ and GNR-AlPcS$_4$ complex, respectively, and FIGS. 19 and 20 are graphs showing fluorescence intensities measured based on the lines shown in FIGS. 17 and 18, respectively.

Referring to FIGS. 17 through 20, it can be seen that, compared to the AlPcS$_4$-treated cell line, the GNR/AlPcS$_4$ complex-treated SCC7 cell line generated a fluorescent signal about 4 times stronger. This indicates that the GNR/AlPcS$_4$ complex is more easily taken up into the cells than the AlPcS$_4$.

Analysis Example 2-4

Quantitative Analysis of Uptake of GNR/AlPcS$_4$ Complex into Cells 90000 cells of a SCC7 (Squamous cell Carcinoma) cell line per well were seeded in a 96 well plate and cultured for 24 hours. Afterwards, the AlPcS$_4$ and the GNR/AlPcS$_4$ complex prepared in Preparation Example 2-4 were diluted with a cell culture medium containing serum to have an equivalent concentration of 5 µM AlPcS$_4$. 600 µl of the diluted solution per well was added, and maintained at 37° C. for 4 hours. Subsequently, after the cell culture medium containing the photosensitizer was removed, the cells were washed three times, and then treated with 200 µl of 0.1% SDS/0.1M NaOH solution for 2 hours for cell lysis. Then, a fluorescence signal of the AlPcS$_4$ generated from this solution was measured (Ex. 660 nm, Em. 690 nm).

Figure 21:
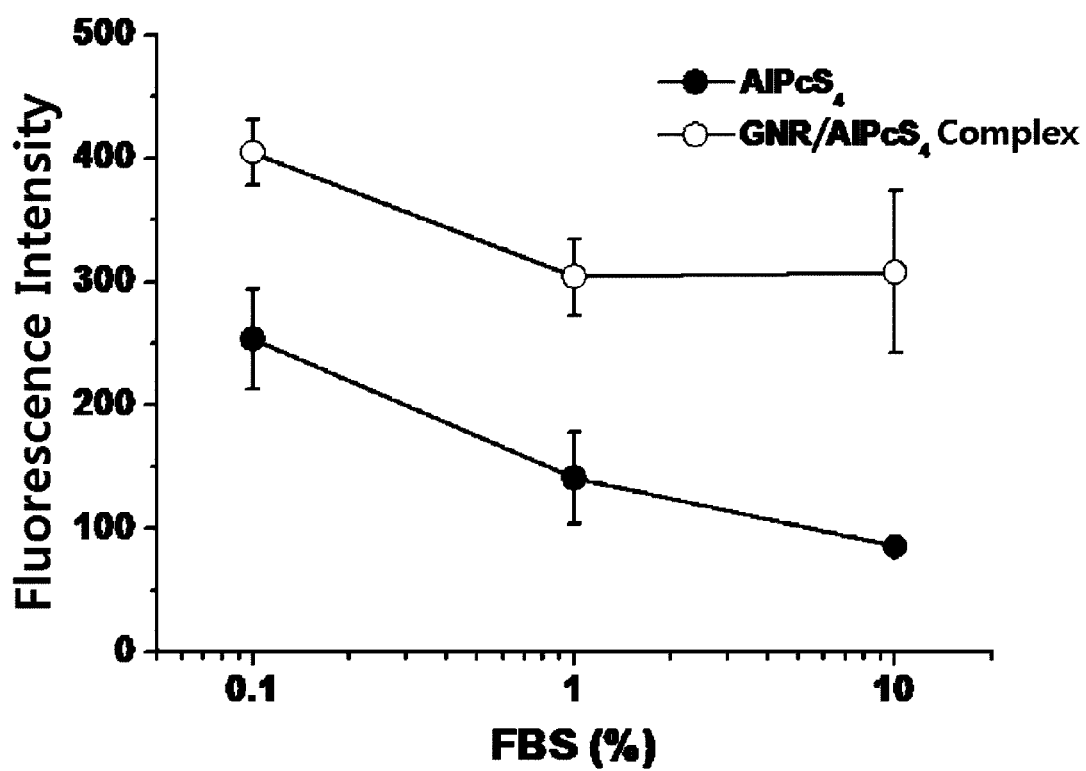
FIG. 21 is a graph showing fluorescence intensity of a cell lysis solution according to an increase in ratio of fetal bovine serum (FBS) in a cell culture medium.

FIG. 21 is a graph showing fluorescence intensity of a cell lysis solution according to an increase in ratio of fetal bovine serum (FBS) in a cell culture medium.

Referring to FIG. 21, in the case of the AlPcS$_4$, as an amount of serum in the cell culture medium was increased, uptake of the photosensitizer into the cells was greatly decreased. However, the GNR/AlPcS$_4$ complex had relatively less of an effect according to the amount of the serum. It can be confirmed that, under the condition of 10% serum, the uptake amount of the GNR/AlPcS$_4$ complex into the cells was about 3.6 times larger than the cells treated with the AlPcS$_4$. It means that a protein component in the serum hindered the uptake of the AlPcS$_4$ into the cells, while the GNR/AlPcS$_4$ complex in which the AlPcS$_4$ was bound to the GNR was inhibited in interaction with the protein in the serum, and more easily taken up into the cells by endocytosis.

Analysis Example 2-5

Cell Viability Test after Photodynamic Therapy 9000 cells of a SCC7 cell line per well were seeded in a 96 well plate, and cultured for 24 hours. After the AlPcS$_4$ and the GNR/AlPcS$_4$ complex prepared in Preparation Example 2-4 were diluted with a cell culture medium to have an equivalent concentration of 5 µM AlPcS$_4$, 200 µl of the diluted solution per well was added and then maintained at 37° C. for 4 hours. For a control group, the same volume of cell culture medium was added to the plate. Afterwards, to remove the photosensitizer which was not taken up into the cell, the cells were washed with a cell culture medium twice, and then a fresh cell culture medium was added. The PDT-treated groups were irradiated with light at 670 nm using laser under conditions of a light dose density of 50 mW/cm$^2$ and light doses of 5 J/cm$^2$ and 10 J/cm$^2$. After 24 hours, cell viability was measured using a cell counting kit-8 (CCK-8, Dojindo Laboratories).

Figure 22:
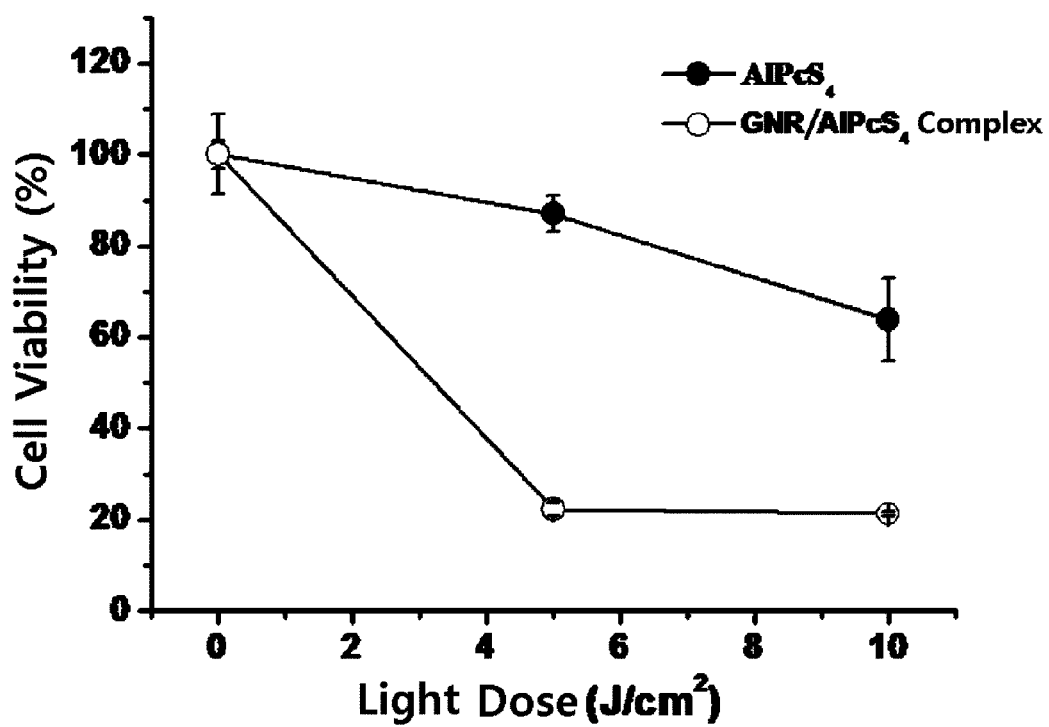
FIG. 22 is a graph showing cell viability based on conditions according to Analysis Example 2-5.

FIG. 22 is a graph showing cell viability according to changes in condition according to Analysis Example 2-5.

Referring to FIG. 22, as a light dose irradiated was increased, the cell viability was decreased. When the AlPcS$_4$ was treated and the photodynamic therapy (10 J/cm$^2$) was performed, 64% of phototoxicity was shown. However, when the GNR/AlPcS$_4$ complex in which the GNR was bound to the AlPcS$_4$ was treated, and the photodynamic therapy was performed, even with a dose of 5 J/cm$^2$, 22% of the cell viability was shown. Therefore, it can be confirmed that the GNR/AlPcS$_4$ complex has a higher efficiency in the photodynamic therapy due to a larger uptake amount of the GNR/AlPcS$_4$ complex into the cells.

Analysis Example 2-6

Evaluation of Near-infrared Fluorescence Imaging and Efficiency of Photodynamic Therapy Using Photosensitizer on Experimental Animal Model $2 \times 10^6$ cells per 100 µl of the SCC7 cell line were injected subcutaneously to hind legs of Balb/c-nu mice of 19 to 22 g to create xenograft tumor models. When a tumor was grown to a size of about 180 cm$^3$, 29 experimental animals were divided into three groups (Day 0) based on the tumor size. Among them, 6 mice were used for near-infrared fluorescence imaging using the photosensitizer, and the other 23 mice were used to observe an inhibitory effect on tumor growth through the photodynamic therapy. A volume of the tumor was calculated with an equation of height×length×width×0.5.

For each of the AlPcS$_4$-treated group and the GNR/AlPcS$_4$ complex-treated group, the drug (each of AlPcS$_4$ and GNR/AlPcS$_4$ complex prepared in Preparation Example 2-4) dissolved in PBS (6.7 mM, pH 7.4, NaCl 154 mM) was injected into a tail vein of a mouse at the dose of 1 mg AlPcS$_4$ equivalent/kilogram body weight. For a control group, only the PBS aqueous solution corresponding to the drug-treated group was injected into a tail vein of a mouse (Day 1). To compare the near-infrared fluorescence image and the accumulated amount in the tumor of the injected photosensitizer, two mice were taken from each group after 24 hours from the treatment of the drug (Day 2), and therefrom fluorescence images of AlPcS$_4$ were obtained using a near-infrared fluorescence image device (IVIS Lumina) (Cy5.5 channel; Ex. filter 615-665 nm, Em. Filter 695-770 nm).

After 24 hours of the drug injection, the photodynamic therapy was performed on the other experimental mice by irradiating tumor sites with laser at 670 nm under conditions of a light dose density of 177 mW/cm$^2$ and a light dose of 60 J/cm$^2$ (Day 2). After the photodynamic therapy, at every 24 hours for 3 days, changes in size of the tumors were measured. On the fifth day after the drug treatment, the diameter of the tumor in the control group exceeded 2 cm, and thus the experiment was completed.

Figure 23:
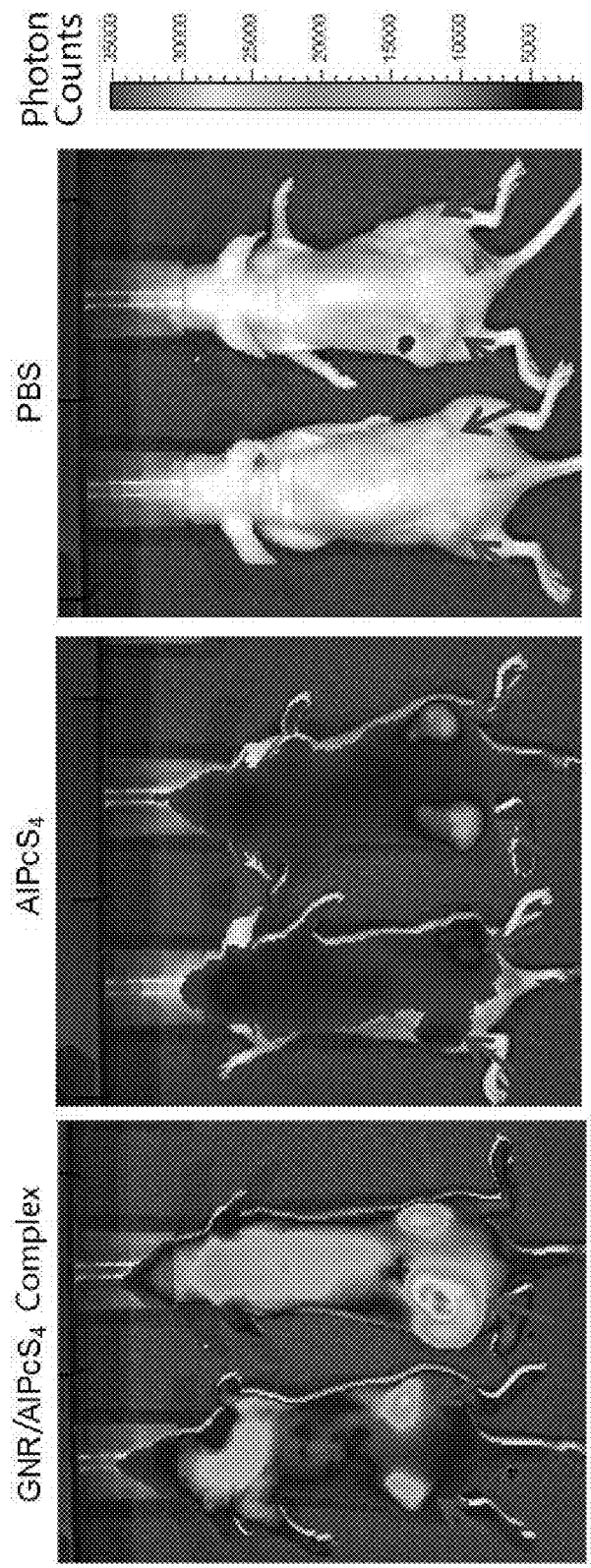
FIG. 23 shows photographs visualizing tumor sites through near-infrared fluorescence imaging.

FIG. 23 shows photographs visualizing tumor sites through near-infrared fluorescence imaging.

Referring to FIG. 23, tumor sites in both the AlPcS$_4$ and the GNR/AlPcS$_4$ complex-treated groups were visualized through the near-infrared fluorescence imaging.

Figure 24:
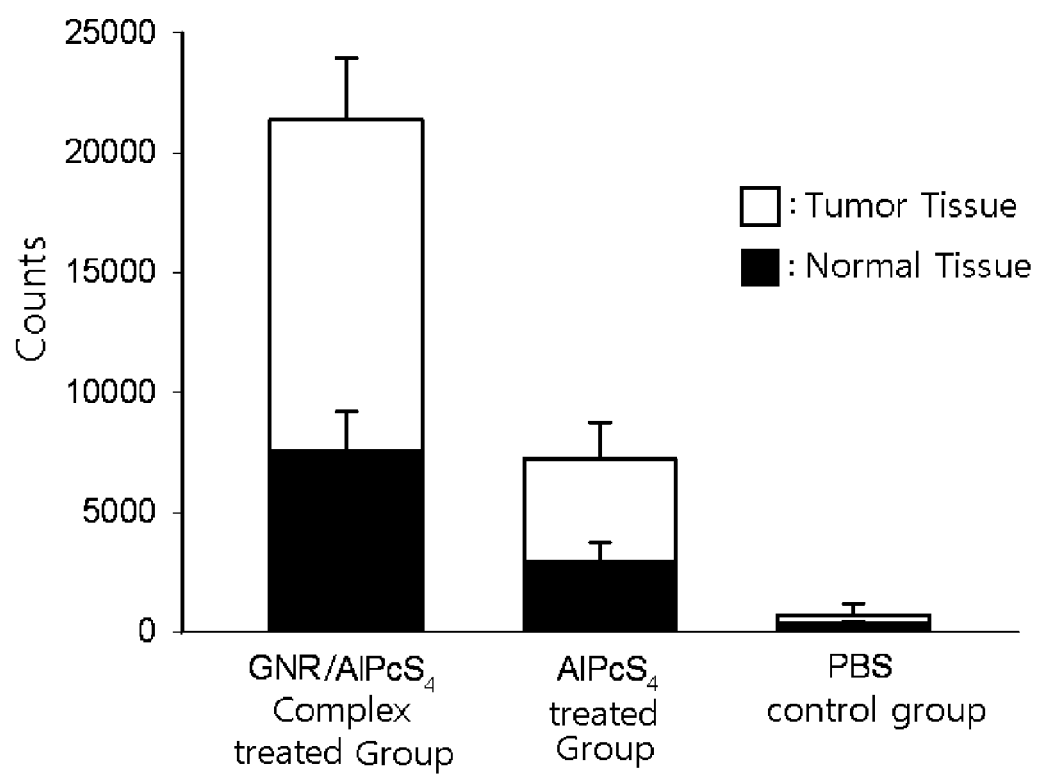
FIG. 24 is a graph showing intensities of an average fluorescence signal (□) in a tumor tissue and an average fluorescence signal (■) in a normal tissue adjacent to the tumor tissue.

FIG. 24 is a graph showing intensities of an average fluorescence signal (□) generated in a tumor tissue and an average fluorescence signal (■) generated in a normal tissue adjacent to the tumor.

Referring to FIG. 24, in the GNR/AlPcS$_4$ complex-treated group, tumor-to-background ratio of the AlPcS$_4$ fluorescence was 2.8, and in the AlPcS$_4$-treated group, tumor-to-background ratio of the AlPcS$_4$ fluorescence was 2.5. In the GNR/AlPcS$_4$ complex-treated group, an average fluorescence signal in tumor of 21365 counts was measured, and in the AlPcS$_4$-treated group, an average fluorescence signal in tumor of 7224 counts was measured. Therefrom, it can be confirmed that the GNR/AlPcS$_4$ complex-treated group has a fluorescence signal 2.9 times higher than the AlPcS$_4$-treated group, and the GNR/AlPcS$_4$ complex-treated group has a higher AlPcS$_4$ concentration in the tumor than the AlPcS$_4$-treated group after 24 hours of the photosensitizer injection.

Figure 25:
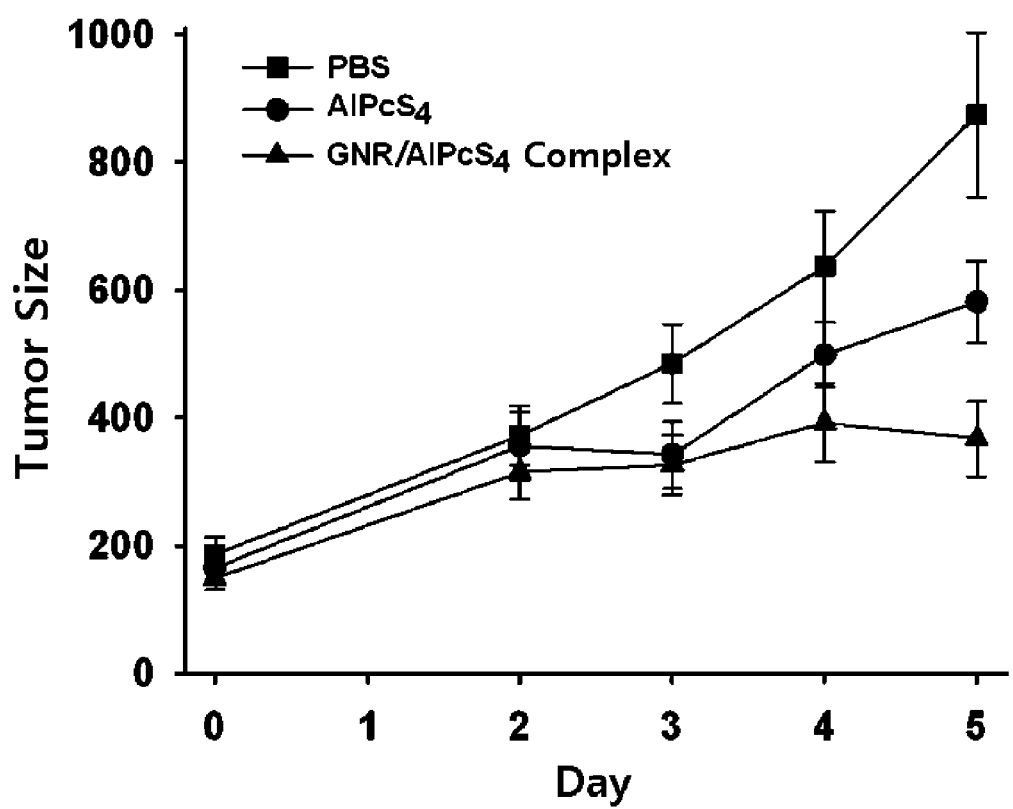
FIG. 25 is a graph showing changes in tumor size after photodynamic therapy is performed on groups treated with the AlPcS$_4$ and GNR-AlPcS$_4$ complex.

FIG. 25 is a graph showing changes in tumor size after the photodynamic therapy was performed on groups treated with the AlPcS$_4$ and GNR-AlPcS$_4$ complex.

Referring to FIG. 25, it can be seen that, in the AlPcS$_4$-treated group, one day after the photodynamic therapy, the tumor size was temporarily decreased (p=0.034), and then increased. However, it was observed that, in the GNR/AlPcS$_4$ complex-treated group, even after 3 days of the photodynamic therapy, tumor growth was still inhibited. In the AlPcS$_4$-treated group, the size of the tumor was 67% of that in the control group on the fifth day (p=0.077), and in the GNR/AlPcS$_4$ complex-treated group, the size of the tumor was 42% of that in the control group on the fifth day (p=0.001). It can be noted that, on the fifth day, a statistically significant difference in tumor size (p=0.011) was shown between the AlPcS$_4$- and GNR/AlPcS$_4$ complex-treated groups. Such a result demonstrates that the GNR/AlPcS$_4$ complex is more easily accumulated in the tumor and exhibits a higher efficiency in the photodynamic therapy than the AlPcS$_4$. The statistical analysis in size of the tumor was performed by a Mann-Whitney test.

While the invention has been shown and described with reference to certain exemplary embodiments thereof, it will be understood by those skilled in the art that various changes in form and details may be made therein without departing from the spirit and scope of the invention as defined by the appended claims.

The invention claimed is:

1. A photosensitizer gold nanoparticle charge complex for photodynamic therapy and fluorescence imaging, comprising:
   a photosensitizer charged with a first charge;
   a gold nanoparticle that transfers resonance energy with the photosensitizer to quench fluorescence of the photosensitizer and singlet oxygen generation; and
   a linker bound to the gold nanoparticle and charged with a second charge having an opposite polarity to the first charge, and bound to the photosensitizer through the charge of the photosensitizer interaction between the first charge and the second charge of the linker,
   wherein the gold nanoparticle has an average length of 34 nm; and
   wherein the linker is a polypeptide containing cysteine (Cys) having the thiol group as a residue on one terminal, and arginine (Arg), lysine (Lys) or histidine (His) having a cation as a residue or aspartic acid (Asp) or glutamic acid (Glu) having an anion as a residue on the other terminal.

2. The complex according to claim 1, wherein the linker has Arg-Arg-Leu-Ala-Cys (RRLAC; SEQ ID NO: 1).

3. A photosensitizer gold nanoparticle charge complex for photodynamic therapy and fluorescence imaging, comprising:
   a photosensitizer charged with a first charge;
   a gold nanoparticle that transfers resonance energy with the photosensitizer to quench fluorescence of the photosensitizer and singlet oxygen generation;
   a linker bound to the gold nanoparticle and charged with a second charge having an opposite polarity to the first charge, and bound to the photosensitizer through the charge of the photosensitizer interaction between the first charge and the second charge of the linker; and a modifying part coating the gold nanoparticle's surface and having a thiol group on one terminal and a functional group charged with a first charge having an opposite polarity to the second charge of the linker on the other terminal, the thiol group chemically bound to the gold nanoparticle to form a thiol-gold bond between the modifying part and the gold nanoparticle, wherein the linker is bound to the gold nanoparticle through the charge interaction between the first charge of the modifying part on the gold nanoparticle and the second charge of the linker, wherein the functional group charged with the first charge of the modifying part is selected from the group consisting of a carboxylate anion, a sulfonate anion, and an ammonium cation, and wherein the gold nanoparticle has an average length of 34 nm.

4. The complex according to claim 3, wherein the modifying part is mercaptosuccinic acid (MSA).

5. The complex according to claim 3, wherein the linker is a polypeptide containing Arg, Lys or His having a cation as a residue, or Asp or Glu having an anion as a residue.

6. The complex according to claim 5, wherein the linker is poly (L-lysine).

7. The complex according to claim 3, wherein the linker is a biocompatible polymer including a substituent selected from the group consisting of a carboxylic acid or a salt thereof, sulfonic acid or a salt thereof, and an amine group.

8. The complex according to claim 7, wherein the biocompatible polymer is selected from the group consisting of a polysaccharide; heparin; hyaluronic acid; gelatin; poly (acrylic acid); polylysine; poly(ethylene imine); chitosan and polyvinylpyrrolidone, which has carboxylic acid or a salt thereof, or sulfonic acid or a salt thereof as a substituent.

9. The complex according to claim 1, wherein the photosensitizer is a porphyrin-based compound or a non-porphyrin compound, the compound is in the form of a free base or metal complex, comprises a substituent selected from the group consisting of a carboxylate anion, a sulfonate anion and an ammonium cation.

10. The complex according to claim 9, wherein the photosensitizer is aluminum tetrasulfophthalocyanine ($AlPcS_4$).

11. The complex according to claim 1, wherein the gold nanoparticle is formed in the shape of a sphere, rod, pyramid, star, or core-shell.

12. The complex according to claim 1, further comprising a hydrophilic polymer bound to the gold nanoparticle or linker.

13. The complex according to claim 12, wherein the hydrophilic polymer is polyethylene glycol (PEG).

14. The complex according to claim 12, further comprising a tumor targeting part bound to the hydrophilic polymer or linker.

15. The complex according to claim 14, wherein the tumor targeting part is selected from the group consisting of an antibody specifically reacting to a tumor, folic acid, a peptide ligand having at least two amino acids, a cyclic arginine-glycine-aspartic acid (RGD) peptide, an RNA aptamer, an siRNA, and an oligonucleotide.

16. The complex according to claim 12, wherein the hydrophilic polymer is selected from the group consisting of methoxy polyethylene glycol (MPEG); methoxy polypropylene glycol; a copolymer of PEG and methoxy polypropylene glycol; dextran; hyaluronic acid; a copolymer of polylactic acid and polyglycolic acid; PEG-diacid; PEG monoamine; MPEG monoamine; MPEG hydrazide; MPEG imidazole; a copolymer of at least two selected from the group consisting of PEG, methoxy polypropylene glycol, PEG-diacid, PEG monoamine, MPEG monoamine, MPEG hydrazide, and MPEG imidazole; and a copolymer selected from the group consisting of PEG and polypeptide, PEG and polysaccharide, PEG and polyamidoamine, PEG and polyethyleneamine, and PEG and polynucleotide.

17. A pharmaceutical composition for photodynamically treating or diagnosing squamous cell carcinoma comprising a photosensitizer-gold nanoparticle charge complex according to claim 1 and a pharmaceutically acceptable carrier.

* * * * *